(12) United States Patent
Kellan et al.

(10) Patent No.: US 8,480,734 B2
(45) Date of Patent: Jul. 9, 2013

(54) INTRAOCULAR LENS WITH ACCOMMODATION

(75) Inventors: Robert E. Kellan, North Andover, MA (US); Paul Koch, East Greenwich, RI (US)

(73) Assignee: Anew Optics, Inc., Bristol, TN (US)

( * ) Notice: Subject to any disclaimer, the term of this patent is extended or adjusted under 35 U.S.C. 154(b) by 0 days.

(21) Appl. No.: 11/965,263

(22) Filed: Dec. 27, 2007

(65) Prior Publication Data

US 2009/0171458 A1    Jul. 2, 2009

(51) Int. Cl.
    *A61F 2/16*    (2006.01)
(52) U.S. Cl.
    USPC ....... 623/6.51; 623/6.37; 623/6.52; 623/6.53; 623/6.54
(58) Field of Classification Search
    USPC .................. 623/6.46, 6.37, 6.51, 6.52, 6.45, 623/6.43, 4.1
    See application file for complete search history.

(56) References Cited

U.S. PATENT DOCUMENTS

| | | |
|---|---|---|
| 3,673,616 A | 7/1972 | Fedorov et al. |
| 3,866,249 A | 2/1975 | Flom |
| 3,906,551 A | 9/1975 | Otter |
| 3,913,148 A | 10/1975 | Potthast |
| 3,975,779 A | 8/1976 | Richards et al. |
| 4,014,049 A | 3/1977 | Richards et al. |
| 4,053,953 A | 10/1977 | Flom et al. |
| 4,073,014 A | 2/1978 | Poler |
| 4,087,866 A | 5/1978 | Choyce et al. |
| 4,092,743 A | 6/1978 | Kelman |
| 4,102,567 A | 7/1978 | Cuffe et al. |
| 4,136,406 A | 1/1979 | Norris |
| 4,141,973 A | 2/1979 | Balazs |
| 4,159,546 A | 7/1979 | Shearing |
| 4,173,281 A | 11/1979 | Trought |
| 4,174,543 A | 11/1979 | Kelman |
| 4,190,049 A | 2/1980 | Hager et al. |
| 4,198,980 A | 4/1980 | Clark |
| 4,215,440 A | 8/1980 | Worst |

(Continued)

FOREIGN PATENT DOCUMENTS

| | | |
|---|---|---|
| CN | 1713862 | 12/2005 |
| DE | 2556665 | 6/1977 |

(Continued)

OTHER PUBLICATIONS

Zaldivar et al.; "The Current Status of Phakic Intraocular Lenses;" International Opthalmology Clinics; vol. 36, No. 4; 1996; pp. 107-111.

(Continued)

*Primary Examiner* — David H Willse
*Assistant Examiner* — Tiffany Shipmon
(74) *Attorney, Agent, or Firm* — Remenick PLLC

(57) ABSTRACT

An accommodating intraocular implant apparatus is disclosed for implantation in the human eye. The apparatus includes an optic portion having a periphery and an optic axis, said optic portion lying substantially within an optic plane transverse to said optic axis; at least one flexible haptic extending from a point on or near the periphery of the optic portion; at least one flexible haptic having a fixation anchor portion distal to the periphery of the optic portion; and at least one flexible haptic having a centering anchor portion. The fixation anchor portion and the centering anchor portion are adapted to couple to a portion of the eye.

19 Claims, 30 Drawing Sheets

U.S. PATENT DOCUMENTS

| | | |
|---|---|---|
| 4,240,163 A | 12/1980 | Galin |
| 4,242,760 A | 1/1981 | Rainin |
| 4,244,060 A | 1/1981 | Hoffer |
| 4,249,271 A | 2/1981 | Poler |
| 4,251,887 A | 2/1981 | Anis |
| 4,254,509 A | 3/1981 | Tennant |
| 4,254,510 A | 3/1981 | Tennant |
| 4,269,307 A | 5/1981 | LaHaye |
| 4,270,230 A | 6/1981 | Poler |
| 4,280,232 A | 7/1981 | Hummel |
| 4,285,072 A * | 8/1981 | Morcher et al. ............. 623/6.51 |
| 4,325,375 A | 4/1982 | Nevyas |
| 4,326,306 A | 4/1982 | Poler |
| 4,349,027 A | 9/1982 | DiFrancesco |
| 4,363,142 A | 12/1982 | Meyer |
| 4,363,143 A | 12/1982 | Callahan |
| 4,366,582 A * | 1/1983 | Faulkner ...................... 623/6.55 |
| 4,370,760 A | 2/1983 | Kelman |
| 4,409,691 A | 10/1983 | Levy |
| 4,423,809 A | 1/1984 | Mazzocco |
| 4,435,855 A | 3/1984 | Pannu |
| 4,441,217 A | 4/1984 | Cozean, Jr. |
| 4,446,581 A | 5/1984 | Blake |
| 4,451,938 A | 6/1984 | Kelman |
| 4,463,458 A | 8/1984 | Seidner |
| 4,468,820 A | 9/1984 | Uhler et al. |
| 4,480,340 A | 11/1984 | Shepard |
| 4,494,254 A | 1/1985 | Lopez |
| 4,504,981 A | 3/1985 | Walman |
| 4,508,216 A | 4/1985 | Kelman |
| 4,517,295 A | 5/1985 | Bracke et al. |
| 4,527,294 A | 7/1985 | Heslin |
| 4,530,117 A | 7/1985 | Kelman |
| 4,534,069 A | 8/1985 | Kelman |
| 4,536,895 A | 8/1985 | Bittner |
| 4,573,998 A | 3/1986 | Mazzocco |
| 4,575,374 A | 3/1986 | Anis |
| 4,576,607 A | 3/1986 | Kelman |
| 4,581,033 A | 4/1986 | Callahan |
| 4,585,456 A | 4/1986 | Blackmore |
| 4,591,358 A | 5/1986 | Kelman |
| 4,608,049 A | 8/1986 | Kelman |
| 4,615,703 A | 10/1986 | Callahan et al. |
| 4,619,256 A | 10/1986 | Horn |
| 4,624,669 A | 11/1986 | Grendahl |
| 4,629,460 A | 12/1986 | Dyer |
| 4,634,423 A | 1/1987 | Bailey, Jr. |
| 4,638,056 A | 1/1987 | Callahan et al. |
| 4,655,775 A | 4/1987 | Clasby, III |
| 4,676,792 A | 6/1987 | Praeger |
| 4,676,794 A | 6/1987 | Kelman |
| 4,684,014 A | 8/1987 | Davenport |
| 4,687,484 A | 8/1987 | Kaplan |
| 4,700,638 A | 10/1987 | Przewalski |
| 4,701,181 A | 10/1987 | Arnott |
| 4,704,123 A | 11/1987 | Smith |
| 4,710,195 A | 12/1987 | Giovinazzo |
| 4,711,638 A * | 12/1987 | Lindstrom ................... 623/6.54 |
| 4,718,906 A | 1/1988 | Mackool |
| 4,736,836 A | 4/1988 | Alongi et al. |
| 4,764,169 A | 8/1988 | Grendahl |
| 4,769,035 A | 9/1988 | Kelman |
| 4,778,464 A | 10/1988 | Sergienko et al. |
| 4,781,719 A | 11/1988 | Kelman |
| 4,787,902 A | 11/1988 | Sheets et al. |
| 4,795,460 A | 1/1989 | Anis |
| 4,795,462 A | 1/1989 | Grendahl |
| 4,804,361 A | 2/1989 | Anis |
| 4,816,032 A | 3/1989 | Hetland |
| 4,828,558 A | 5/1989 | Kelman |
| 4,834,750 A | 5/1989 | Gupta |
| 4,842,600 A | 6/1989 | Feaster |
| RE33,039 E | 8/1989 | Arnott |
| 4,852,566 A | 8/1989 | Callahan et al. |
| 4,863,462 A | 9/1989 | Fedorov et al. |
| 4,863,463 A | 9/1989 | Tjan |
| 4,863,465 A | 9/1989 | Kelman |
| 4,871,363 A | 10/1989 | Kelman |
| 4,872,876 A | 10/1989 | Smith |
| 4,878,911 A | 11/1989 | Anis |
| 4,888,012 A | 12/1989 | Horn |
| 4,919,130 A | 4/1990 | Stoy et al. |
| 4,923,296 A | 5/1990 | Erickson |
| 4,932,970 A | 6/1990 | Portney |
| 4,950,290 A | 8/1990 | Kamerling |
| 4,994,080 A | 2/1991 | Shepard |
| 4,995,714 A | 2/1991 | Cohen |
| 5,002,568 A | 3/1991 | Katzen |
| 5,019,098 A | 5/1991 | Mercier |
| 5,047,052 A | 9/1991 | Dubroff |
| 5,076,684 A | 12/1991 | Simpson et al. |
| 5,098,444 A | 3/1992 | Feaster |
| 5,100,226 A | 3/1992 | Freeman |
| 5,108,429 A | 4/1992 | Wiley |
| 5,118,452 A | 6/1992 | Lindsey et al. |
| 5,123,905 A | 6/1992 | Kelman |
| 5,133,747 A | 7/1992 | Feaster |
| 5,133,749 A | 7/1992 | Nordan |
| 5,166,711 A | 11/1992 | Portney |
| 5,171,320 A | 12/1992 | Nishi |
| 5,176,686 A | 1/1993 | Poley |
| 5,178,636 A | 1/1993 | Silberman |
| 5,192,319 A | 3/1993 | Worst |
| 5,197,981 A | 3/1993 | Southard |
| 5,199,559 A | 4/1993 | Dark |
| 5,229,797 A | 7/1993 | Futhey et al. |
| 5,236,452 A | 8/1993 | Nordan |
| 5,258,025 A | 11/1993 | Fedorov et al. |
| 5,266,074 A | 11/1993 | Nishi et al. |
| 5,281,227 A | 1/1994 | Sussman |
| 5,361,780 A | 11/1994 | Kellan |
| 5,366,501 A | 11/1994 | Langerman |
| 5,370,652 A | 12/1994 | Kellan |
| 5,405,386 A | 4/1995 | Rheinish et al. |
| 5,425,734 A | 6/1995 | Blake |
| D360,068 S | 7/1995 | Hambleton et al. |
| 5,443,506 A | 8/1995 | Garabet |
| 5,468,246 A | 11/1995 | Blake |
| 5,476,512 A | 12/1995 | Sarfarazi |
| 5,476,514 A | 12/1995 | Cumming |
| 5,480,428 A | 1/1996 | Fedorov et al. |
| 5,489,302 A | 2/1996 | Skottun |
| 5,496,366 A * | 3/1996 | Cumming ..................... 128/898 |
| 5,507,806 A | 4/1996 | Blake |
| 5,522,890 A | 6/1996 | Nakajima et al. |
| 5,549,670 A | 8/1996 | Young et al. |
| 5,593,436 A | 1/1997 | Langerman |
| 5,628,794 A | 5/1997 | Lindstrom |
| 5,643,275 A | 7/1997 | Blake |
| D382,399 S | 8/1997 | Hambleton et al. |
| 5,674,282 A | 10/1997 | Cumming |
| 5,682,223 A | 10/1997 | Menezes et al. |
| 5,697,973 A | 12/1997 | Peyman |
| 5,709,220 A | 1/1998 | Kellan |
| 5,713,958 A | 2/1998 | Weiser |
| 5,772,667 A | 6/1998 | Blake |
| 5,782,911 A | 7/1998 | Herrick |
| 5,800,532 A | 9/1998 | Lieberman |
| 5,847,802 A | 12/1998 | Menezes et al. |
| 5,855,605 A | 1/1999 | Herrick |
| 5,919,229 A | 7/1999 | Portney |
| 5,928,282 A | 7/1999 | Nigam |
| 5,947,976 A | 9/1999 | Van Noy et al. |
| 5,976,150 A | 11/1999 | Copeland |
| 6,010,510 A | 1/2000 | Brown |
| 6,013,101 A | 1/2000 | Israel |
| 6,015,435 A | 1/2000 | Valunin |
| 6,051,024 A | 4/2000 | Cumming |
| 6,083,261 A | 7/2000 | Callahan et al. |
| 6,090,141 A | 7/2000 | Lindstrom |
| 6,096,077 A | 8/2000 | Callahan et al. |
| 6,110,202 A | 8/2000 | Barraquer et al. |
| 6,120,148 A | 9/2000 | Fiala et al. |
| 6,129,723 A | 10/2000 | Anderson |
| 6,142,999 A | 11/2000 | Brady et al. |
| 6,152,958 A | 11/2000 | Nordan |
| 6,197,059 B1 | 3/2001 | Cumming |

| | | |
|---|---|---|
| 6,203,549 B1 | 3/2001 | Waldock |
| 6,224,628 B1 | 5/2001 | Callahan et al. |
| 6,241,777 B1 | 6/2001 | Kellan |
| 6,261,321 B1 * | 7/2001 | Kellan .................... 623/6.51 |
| 6,277,146 B1 | 8/2001 | Peyman et al. |
| 6,299,641 B1 | 10/2001 | Woods |
| 6,398,786 B1 | 6/2002 | Sesic |
| 6,443,985 B1 | 9/2002 | Woods |
| 6,447,519 B1 | 9/2002 | Brady |
| 6,461,384 B1 | 10/2002 | Hoffmann |
| 6,488,707 B1 | 12/2002 | Callahan et al. |
| 6,488,709 B1 | 12/2002 | Barrett |
| 6,494,911 B2 | 12/2002 | Cumming |
| 6,517,577 B1 | 2/2003 | Callahan et al. |
| 6,533,813 B1 | 3/2003 | Lin et al. |
| 6,537,283 B2 | 3/2003 | Van Noy |
| 6,605,093 B1 | 8/2003 | Blake |
| 6,622,855 B1 | 9/2003 | Callahan et al. |
| 6,623,522 B2 | 9/2003 | Nigam |
| 6,645,246 B1 | 11/2003 | Weinschenk, III |
| 6,666,887 B1 | 12/2003 | Callahan et al. |
| 6,749,633 B1 | 6/2004 | Lorenzo |
| 6,786,928 B2 | 9/2004 | Callahan et al. |
| 6,797,004 B1 | 9/2004 | Brady |
| 6,800,091 B2 | 10/2004 | Callahan et al. |
| 6,921,415 B2 | 7/2005 | Callahan et al. |
| 6,976,989 B1 | 12/2005 | Vincent |
| 7,037,328 B2 | 5/2006 | Vincent |
| 7,037,338 B2 | 5/2006 | Nagamoto |
| 7,063,723 B2 | 6/2006 | Ran |
| 7,125,422 B2 | 10/2006 | Woods |
| 7,179,292 B2 | 2/2007 | Worst |
| 7,220,279 B2 | 5/2007 | Nun |
| 7,223,288 B2 | 5/2007 | Zhang |
| 7,279,006 B2 | 10/2007 | Vincent |
| 7,354,451 B2 | 4/2008 | Koch |
| 7,503,938 B2 | 3/2009 | Phillips |
| 7,713,299 B2 | 5/2010 | Brady et al. |
| 8,043,372 B2 | 10/2011 | Bumbalough |
| 2001/0001836 A1 * | 5/2001 | Cumming .................... 623/6.37 |
| 2001/0012964 A1 | 8/2001 | Lang |
| 2001/0044657 A1 * | 11/2001 | Kellan .................... 623/6.51 |
| 2002/0055777 A1 * | 5/2002 | Cumming et al. .......... 623/6.37 |
| 2002/0072673 A1 | 6/2002 | Yamamoto |
| 2002/0095212 A1 | 7/2002 | Boehm |
| 2002/0103536 A1 | 8/2002 | Landreville et al. |
| 2002/0120331 A1 | 8/2002 | Galin et al. |
| 2002/0161437 A1 | 10/2002 | Zhou et al. |
| 2002/0193877 A1 | 12/2002 | Hoffmann et al. |
| 2003/0033013 A1 | 2/2003 | Callahan |
| 2003/0050695 A1 | 3/2003 | Lin et al. |
| 2003/0065387 A1 | 4/2003 | Callahan et al. |
| 2003/0078655 A1 | 4/2003 | Callahan |
| 2003/0114927 A1 | 6/2003 | Nagamoto |
| 2003/0130732 A1 | 7/2003 | Sarfarazi |
| 2003/0135273 A1 | 7/2003 | Callahan |
| 2003/0149480 A1 | 8/2003 | Shadduck et al. |
| 2004/0215340 A1 | 10/2004 | Messner |
| 2004/0230300 A1 * | 11/2004 | Bandhauer et al. .......... 623/6.37 |
| 2004/0236423 A1 | 11/2004 | Zhang et al. |
| 2004/0249456 A1 * | 12/2004 | Cumming .................... 623/6.37 |
| 2005/0033308 A1 | 2/2005 | Callahan |
| 2005/0107875 A1 * | 5/2005 | Cumming .................... 623/6.37 |
| 2005/0251253 A1 | 11/2005 | Gross |
| 2006/0047339 A1 | 3/2006 | Brown |
| 2006/0047340 A1 | 3/2006 | Brown |
| 2006/0100704 A1 | 5/2006 | Blake |
| 2006/0142781 A1 | 6/2006 | Pynson et al. |
| 2006/0235515 A1 | 10/2006 | Chassain |
| 2006/0247767 A1 | 11/2006 | Koch |
| 2006/0293694 A1 | 12/2006 | Futamura |
| 2007/0093892 A1 | 4/2007 | Mackool |
| 2007/0239274 A1 | 10/2007 | Kellan |
| 2008/0161913 A1 | 7/2008 | Brady et al. |
| 2008/0281417 A1 | 11/2008 | Nagamoto |
| 2009/0171458 A1 | 7/2009 | Kellan et al. |
| 2009/0248031 A1 | 10/2009 | Ichinohe et al. |
| 2010/0131059 A1 | 5/2010 | Callahan et al. |
| 2010/0131061 A1 | 5/2010 | Callahan et al. |
| 2010/0179652 A1 | 7/2010 | Yamamoto |
| 2010/0228260 A1 | 9/2010 | Callahan et al. |
| 2011/0191086 A1 | 8/2011 | Callahan |
| 2011/0313522 A1 | 12/2011 | Hayes |
| 2011/0313523 A1 | 12/2011 | Hayes |

FOREIGN PATENT DOCUMENTS

| | | |
|---|---|---|
| DE | 2717706 | 10/1978 |
| DE | 3722910 | 1/1989 |
| DE | 4030005 | 3/1992 |
| DE | 4040005 | 6/1992 |
| EP | 1961399 | 4/1991 |
| FR | 2653325 | 4/1991 |
| FR | 2666503 | 3/1992 |
| FR | 2687304 | 8/1993 |
| GB | 2029235 | 3/1980 |
| GB | 2124500 | 2/1984 |
| GB | 2165456 | 4/1986 |
| JP | 2000-245755 | * 9/2000 |
| SU | 1377086 | 2/1988 |
| WO | WO98/17205 | 4/1998 |
| WO | WO99/29266 | 6/1999 |
| WO | WO00/78252 | 12/2000 |
| WO | WO03017867 | 6/2003 |
| WO | WO 2007/117476 | 10/2007 |
| WO | WO2007117476 | 10/2007 |
| WO | WO 2007/134019 A2 | 11/2007 |
| WO | WO2007134019 | 11/2007 |

OTHER PUBLICATIONS

Neuhann; "Corneal or Lens Refractive Surgery?" Journal of Refractive Surgery; vol. 14; May/Jun. 1998; pp. 272-279.

Rosen et al.; "Staar Collamer Posterior Chamber Phakic Intraocular Lens to Correct Myopia and Hyperopia;" J. Cataract Refract. Surg.; vol. 24; May 1998; pp. 596-606.

Sanders et al.; "Implantable Contact Lens for Moderate to High Myopia: Phase I FDA Clinical Study with 6 Month Follow-Up;" J. Cataract Refract. Surg.; vol. 24; May 1998; pp. 607-6111.

Japan Office Action for Japanese Application 2009-504268, dated Apr. 24, 2012.

Chinese Decision of Rejection for Chinese Application 200780020967.4, dated May 28, 2012.

Chinese Office Action for Chinese Application 200780020967.4 dated Apr. 12, 2011.

Austria Examination Report for Austrian Application 200807369-4 dated Mar. 10, 2010.

PCT Search Report for PCT/US2009/065955 dated Jan. 27, 2010.

PCT Patentability Report for PCT/US2009/065955 dated Jan. 27, 2010.

PCT Search Report for PCT/US2009/065960 dated Jan. 27, 2010.

PCT Patentability Report for PCT/US2009/065960 dated Jan. 27, 2010.

PCT Search Report for PCT/US2007/008328 dated Jun. 19, 2008.

PCT Patentability Report for PCT/US2007/008328 dated Jun. 19, 2008.

PCT Search Report for PCT/US2008/088430 dated Aug. 11, 2009.

PCT Patentability Report for PCT/US2008/088430 dated Aug. 11, 2009.

PCT Search Report for PCT/US2010/026230 dated May 19, 2010.

PCT Patentabilty Report for PCT/US2010/026230 dated May 19, 2010.

PCT Search Report for PCT/US2006/16221 dated May 10, 2007.

PCT Patentability Report for PCT/US2006/16221 dated May 10, 2007.

PCT Search Report for PCT/US2011/37583 dated Nov. 15, 2011.

PCT Patentabilty Report for PCT/US2011/37583 dated Nov. 15, 2011.

Austria Examination Report for Austrian Application 2009319753, dated Aug. 29, 2012.

PCT Search Report and Patentability Report for PCT/US12/40732, dated Sep. 18, 2012.

EPO Search Report for PCT/US2007/008328, dated Oct. 26, 2012.

EPO Opinion for PCT/US2007/008328, dated Oct. 26, 2012.

* cited by examiner

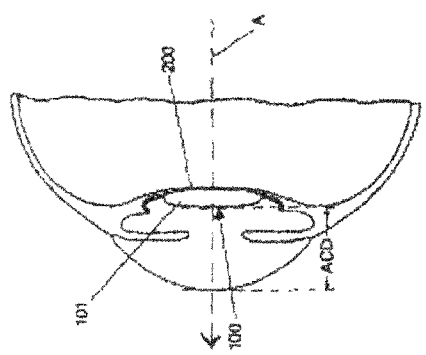
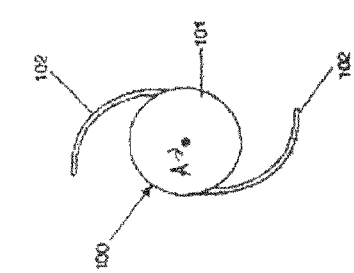
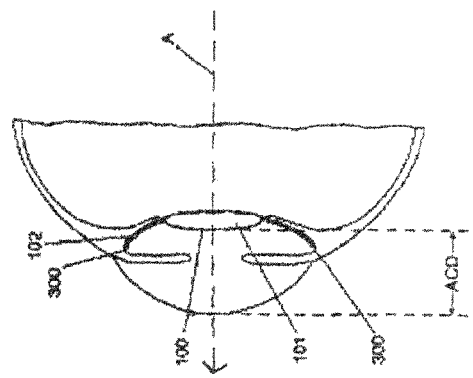

INTRAOCULAR LENS WITH ACCOMMODATION

BACKGROUND

The present disclosure relates to implantable intraocular lenses.

Implantation of artificial lenses into the human eye has been a standard technique for many years, both to replace the natural crystalline lens (aphakic eye) and to supplement and correct refractive errors of the natural lens (phakic eye). However, accommodation provided by such replacement lenses is minimal or non-existent.

The crystalline lens is a transparent structure that focuses light in the human eye. Opacification of the lens known as cataract formation is a common cause of poor vision in the elderly, and can be corrected surgically.

Modern cataract surgery is performed by manual extracapsular cataract extraction, or by phacoemulsification. In both operations an opening is made in the anterior capsule to allow removal of the lens. The capsular bag remnant, however, is left in situ to provide support for an intraocular lens implant which is inserted following removal of the cataract, to replace the focusing power of the natural crystalline lens.

It is known to provide an intraocular lens implant which typically comprises a central focusing element, known as an optic, and peripheral support structure, known as a haptic. The optic and the haptic of the intraocular lens may be manufactured from transparent rigid plastics material such as polymethyl methacrylate, or from flexible plastics material such as silicone or hydrogel. Intraocular lens implants manufactured from flexible material are typically preferable to those made of rigid material because the lens may be folded to allow insertion through a small incision in the sclera or outercoat of the eye and is then required to unfold to its original dimension.

The optic and haptic of the intraocular lens may be manufactured from the same material as a single piece unit or the haptic may be attached to the optic by a variety of mechanisms. There may be one or a plurality of haptics attached to the optic, although the most common configuration includes an optic with two outwardly extending haptics. The purpose of the haptic or haptics is to provide optimal centration of the optic as well as a means of fixation of the implant within the eye (e.g. within a capsular bag remnant of the original lens following cataract or lens extraction). It is preferable that the haptics conform to the periphery of the capsular bag to provide a larger surface area of contact between the intraocular lens implant and the capsular bag and to ensure centration of the optic.

It is also possible to implant a lens in front of the anterior capsule behind the iris with the haptics resting in the region between the root of the iris and cilairy processes, known as the ciliary sulcus.

Intraocular lenses may also be inserted in phakic eyes to correct refractive errors, such as myopia or hyperopia, in front of the crystalline lens behind the iris with the haptic providing support in the cilairy sulcus. Furthermore, as an alternative site of implantation in phakic eyes, intraocular lenses may be inserted in front of the iris in the anterior chamber with the haptics resting in the angle of the anterior chamber.

An example of a conventional intraocular lens 100 in accordance with the prior art shown in FIG. 1 comprises a central optic 101, and two haptics 102 connected to the central optic 101. As shown in FIG. 2, the conventional intraocular lens 100 is mounted in the capsular bag 200 of a human eye with the central optic 101 coaxially aligned with a vision axis A of the eye. However, an anterior chamber distance (ACD) is fixed (i.e., the lens 100 does not accommodate), the central optic 101 is not moveable along the vision axis A of the eye, and the refractive power of the lens cannot be adjusted. As shown in FIG. 3, the conventional intraocular lens 100 can also be mounted in the ciliary sulcus 300 of the human eye when the capsular bag 200 is not complete. The two haptics 102 of the conventional intraocular lens 100 are settled on the ciliary sulcus 300. However, the anterior chamber distance (ACD) is fixed, and the refractive power thereof cannot be adjusted.

Intraocular lenses differ with respect to their accommodation capability, and their placement in the eye. Accommodation is the ability of an intraocular lens to accommodate, which is to focus the eye for near and distant vision. Natural accommodation in a normal human eye involves shaping of the natural crystalline lens by automatic contraction and relaxation of the ciliary muscle of the eye by the brain to focus the eye at different distances. Ciliary muscle relaxation shapes the natural lens for distant vision. Ciliary muscle contraction shapes the natural lens for near vision.

Most non-accommodating implanted lenses have single focus optics which focus the eye at a certain fixed distance only and require the wearing of eye glasses to change the focus. Other non-accommodating lenses have multifocal optics which image both near and distant objects on the retina of the eye and provide both near vision and distant vision sight without eyeglasses. Multifocal intraocular lenses, however, suffer from the disadvantage that each bifocal image represents only about 40% of the available light and the remaining 20% of the light is lost in scatter.

What is still desired is a new and improved intraocular lens implant wherein the coaxial position of the central optic along the vision axis may be changed by control of the user and accommodate automatically. Preferably, the new and improved intraocular lens implant will utilize the ciliary muscle action and to effect accommodation movement of the lens optic along the vision axis of the eye between a distant vision position to a near vision position.

SUMMARY

The inventors have realized that an intraocular implant device may provide accommodation. For example, an implant may include an optic portion, e.g. a lens, positioned along a vision axis of the eye. At least one centering anchor portion of the implant is received by the ciliary sulcus of the eye, and at least one fixation anchor portion is received by the ciliary body, ciliary muscle, or zonules. One or more haptics connect the centering and fixation anchor portions to the optic portion. The fixation anchor portions move in response to the natural action (i.e. contraction or relaxation) of the ciliary body/muscle. This motion is transferred by one or more haptics to the optic portion, moving it along the vision axis, and thereby providing accommodation. During this action, the centering anchor portions received by the sulcus remain substantially stationary, and operate, along with one or more haptics to maintain the alignment of the optic portion with the vision axis.

In one aspect, disclosed is an accommodating intraocular implant apparatus for implantation in the human eye, which includes: an optic portion having a periphery and an optic axis, the optic portion lying substantially within an optic plane transverse to the optic axis; at least one flexible haptic extending from a point on or near the periphery of the optic portion; at least one flexible haptic having a fixation anchor portion distal to the periphery of the optic portion; and at least one flexible haptic having a centering anchor portion. the fixation anchor portion and the centering anchor portion are adapted to couple to a portion of the eye.

In some embodiments, the optic axis is adapted for coaxial alignment with a vision axis of the eye. In some embodiments, at least one centering anchor portion is adapted to couple to the ciliary sulcus of the eye; at least one fixation anchor portion is adapted to couple to one of: a ciliary body, a ciliary muscle, or a ciliary zonule of the eye; at least one flexible haptic is adapted to connect the optic portion to the at least one centering anchor portion to maintain the coaxial alignment of the optic axis with the vision axis, and at least one haptic is configured to connect the optic portion to the at least one fixation anchor portion and, in response to ciliary muscle action in the eye, move the optic portion along the vision axis to provide accommodation.

In some embodiments, at least one flexible haptic includes at least one centering anchor portion and a least one fixation anchor portion. In some embodiments, the at least one flexible haptic includes a first connecting portion extending from the periphery of the optic portion to one of: the at least one fixation anchor portion and the at least one centering anchor point. The at least one flexible haptic may include a second connecting portion extending between the at least one fixation anchor portion and the at least one centering anchor portion. In some such embodiments, the periphery of the optic portion includes a circumferential edge which lies substantially in the optic plane, and the first connecting portion extends from the circumferential edge to the at least one fixation anchor portion at an angle to the optic plane. In some embodiments, the first connecting portion extends away from the optic plane on a side of the optic plane adapted to face towards the posterior of the eye. In some embodiments, the at least one centering anchor portion lies substantially within the optic plane.

In some embodiments, at least one flexible haptic includes a closed loop type haptic extending from the periphery of the optic portion, an open loop type haptic extending from the periphery of the optic portion, a straight type haptic extending from the periphery of the optic portion, or a includes a paddle type haptic extending from the periphery of the optic portion.

In some embodiments, at least one flexible haptic includes at least one fixation anchor portion, the anchor portion extending from a surface of the at least one flexible haptic adapted to face the anterior portion of the human eye.

In some embodiments, at least one haptic includes the at least one fixation anchor portion, the anchor portion extending from a surface of the at least one flexible haptic adapted to face the posterior portion of the human eye.

In some embodiments, the apparatus includes M centering anchoring portions, where M is a positive integer, and N fixation anchor portions, where N is a positive integer. For example, in some embodiments, M is greater than 1 and N is greater than 1.

In some embodiments, N is greater than 3. In some embodiments, N is greater than 7.

Some embodiments include multiple flexible haptics, each of the multiple flexible haptics configured to connect at least one centering anchor portion or at least one fixation anchor portion to the periphery of the optic portion.

In some embodiments, at least one flexible haptic is integral with the optic portion.

In some embodiments, the intraocular implant is foldable.

In some embodiments, the implant includes a material selected from the group consisting of: hydrogel, collagen, collamar, collagel, acrylate polymers, methacrylate polymers, silicone polymers, and composites thereof.

Some embodiments include a first flexible haptic and a second flexible haptic, each of the haptics including: a first connecting portion extending between the periphery of the optic portion and a first fixation anchor portion, a second connecting portion extending between the first fixation anchor portion and a centering anchor portion, a third connecting portion extending between the centering anchor portion and a second fixation anchor point; a fourth connecting portion extending between the second fixation anchor portion and the periphery of the optic portion. In some embodiments, the periphery of the optic portion includes a circumferential edge which lies substantially in the optic plane, and the first and fourth connecting portions extend from the circumferential edge to at an angle to the optic plane. In some embodiments, the first and fourth connecting portion extend away from the optic plane on a side of the optic plane adapted to face towards the posterior of the eye when the intraocular implant is implanted.

In some embodiments, the at least one fixation anchor portion includes one of: a serrated portion, a wedge shaped portion, a cylindrical portion, multiple connected wedge shaped portions, multiple connected cylindrical portions, a bar shaped portion.

In another aspect, a method for correcting vision in a human eye is disclosed including implanting an accommodating intraocular implant in the eye. The intraocular implant being of any of the types described above. In some embodiments, the implanting includes: coupling at least one centering anchor portion to the ciliary sulcus of the eye; coupling at least one fixation anchor portion to one of: a ciliary body, a ciliary muscle, a ciliary zonule of the eye.

In some embodiments, the implanting further includes: making an incision in the eye; folding the accommodating intraocular implant into a folded state small enough to pass through the incision; passing the accommodating intraocular implant through the incision to a desired position within the eye; and unfolding the accommodating intraocular implant to an unfolded state suitable for coupling to the eye. Some embodiments further include removing the natural crystalline lens of the eye.

Embodiments may include any of the above described features alone or in combination.

BRIEF DESCRIPTION OF THE DRAWINGS

FIG. 1 is a front elevation view of a conventional intraocular lens in accordance with the prior art;

FIG. 2 is a side elevation view of the intraocular lens of FIG. 1 shown mounted in a capsular bag of a human eye and coaxially aligned with an imaginary vision axis of the eye;

FIG. 3 is a side elevation view of the intraocular lens of FIG. 1 shown mounted in a ciliary sulcus of a human eye and coaxially aligned with an imaginary vision axis of the eye;

FIG. 7i shows a front view of implant 10;

FIG. 12b shows a front view of implant 10 with an exemplary haptic configuration similar to that given in FIG. 12a.

FIG. 13b shows a front view of implant 10 with an exemplary haptic configuration similar to that given in FIG. 13a.

FIG. 14b shows a front view of implant 10 with an exemplary haptic configuration similar to that given in FIG. 14a.

FIG. 16b shows a front view of implant 10 with an exemplary haptic configuration similar to that given in FIG. 16a.

Like reference numerals and labels refer to like elements throughout the figures.

DETAILED DESCRIPTION

In the eye, the natural lens of the eye separates the aqueous humor from the vitreous body. The iris separates the region between the cornea or anterior of the eye and the lens into an anterior chamber and a posterior chamber. The natural crystalline lens is contained in a membrane known as the capsule or capsular bag. When the natural lens is removed from the eye, the capsule may also be removed (intracapsular excision), or the anterior portion of the capsule may be removed with the natural crystalline lens, leaving the posterior portion of the capsule intact (extracapsular extraction), often leaving small folds or flaps from the anterior portion of the capsule. In an intraocular implant, an artificial lens may be inserted in the anterior chamber, the posterior chamber, or the capsular sac.

FIGS. 4 through 7j through show an exemplary embodiment of an accommodating intraocular implant 10 according to the present disclosure for implantation in the human eye. Throughout the figures, the orientation with respect to the eye is shown relative to vision axis A, which appears in side views as a dotted arrow pointing toward the anterior (front) portion of the eye. The axis A appears in front views as a black dot, indicating that the anterior facing point of the arrow would pierce through the page toward the reader in the front view. In each figure showing a front view, an orientation is assumed where the top of patient's head would be towards the top of the figure ("twelve o'clock"), while the patient's feet would be toward the bottom of the figure ("six o'clock").

Figure 4:
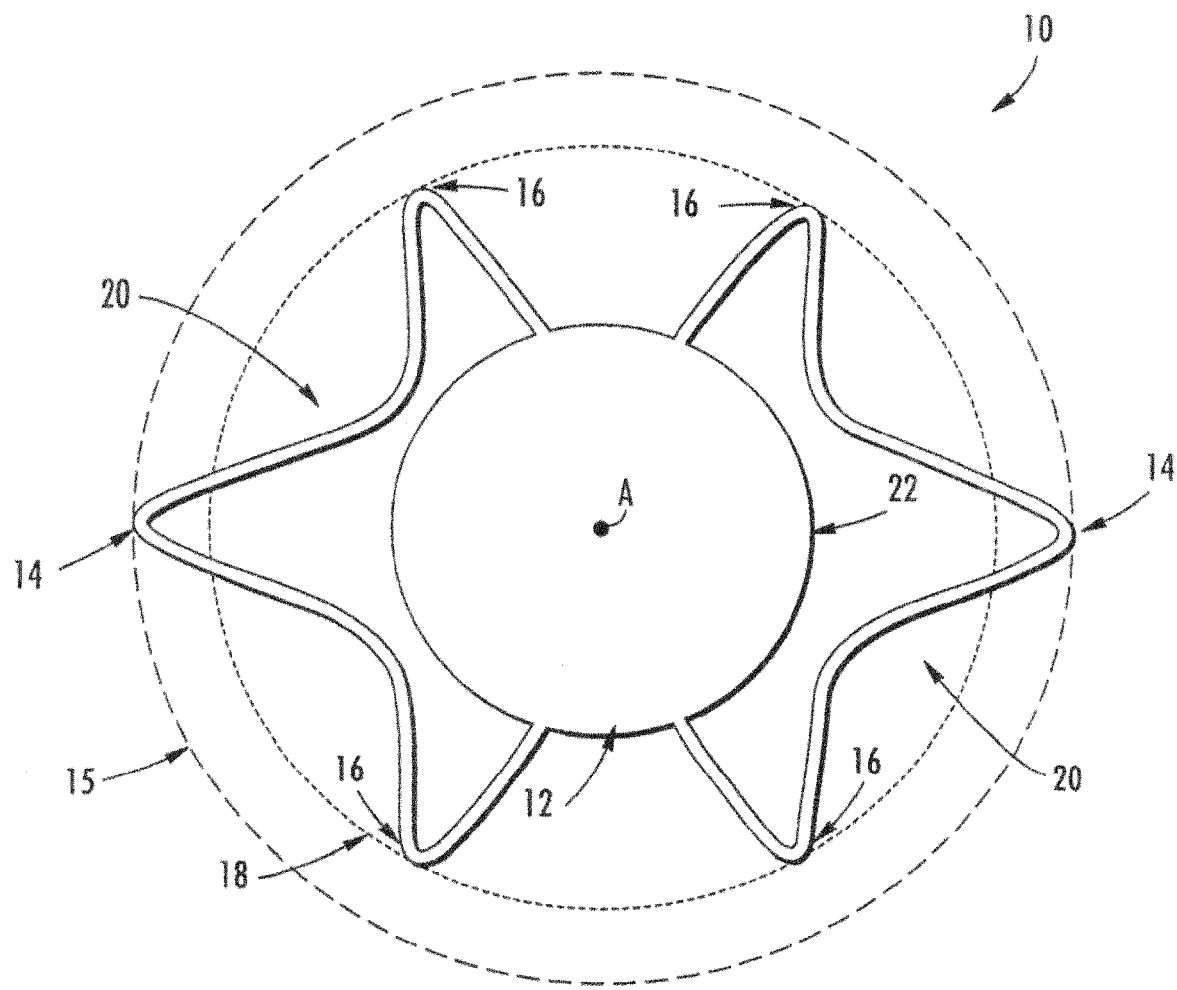
FIG. 4 is a front view of an exemplary intraocular implant 10.

Referring to FIG. 4, implant 10 includes an optic portion 12 adapted for coaxial alignment with the vision axis A of the human eye. Two centering anchor portions 14 are received by the ciliary sulcus 15 of the eye. Four fixation anchor portions 16 are received by the ciliary body/muscle 18 of the eye, (e.g., in the zonules positioned closely to the ciliary body). The anchor points are connected to the periphery (e.g. circumferential edge) 22 of optic portion 12 by two haptics 20. Each haptic 20 forms a closed loop (e.g. as shown with a distorted "C" or "U" shape) with the optic portion 12, and connects two fixation anchor portions 16 and one centering anchor portion 14 to the optic portion 12.

Figure 5:
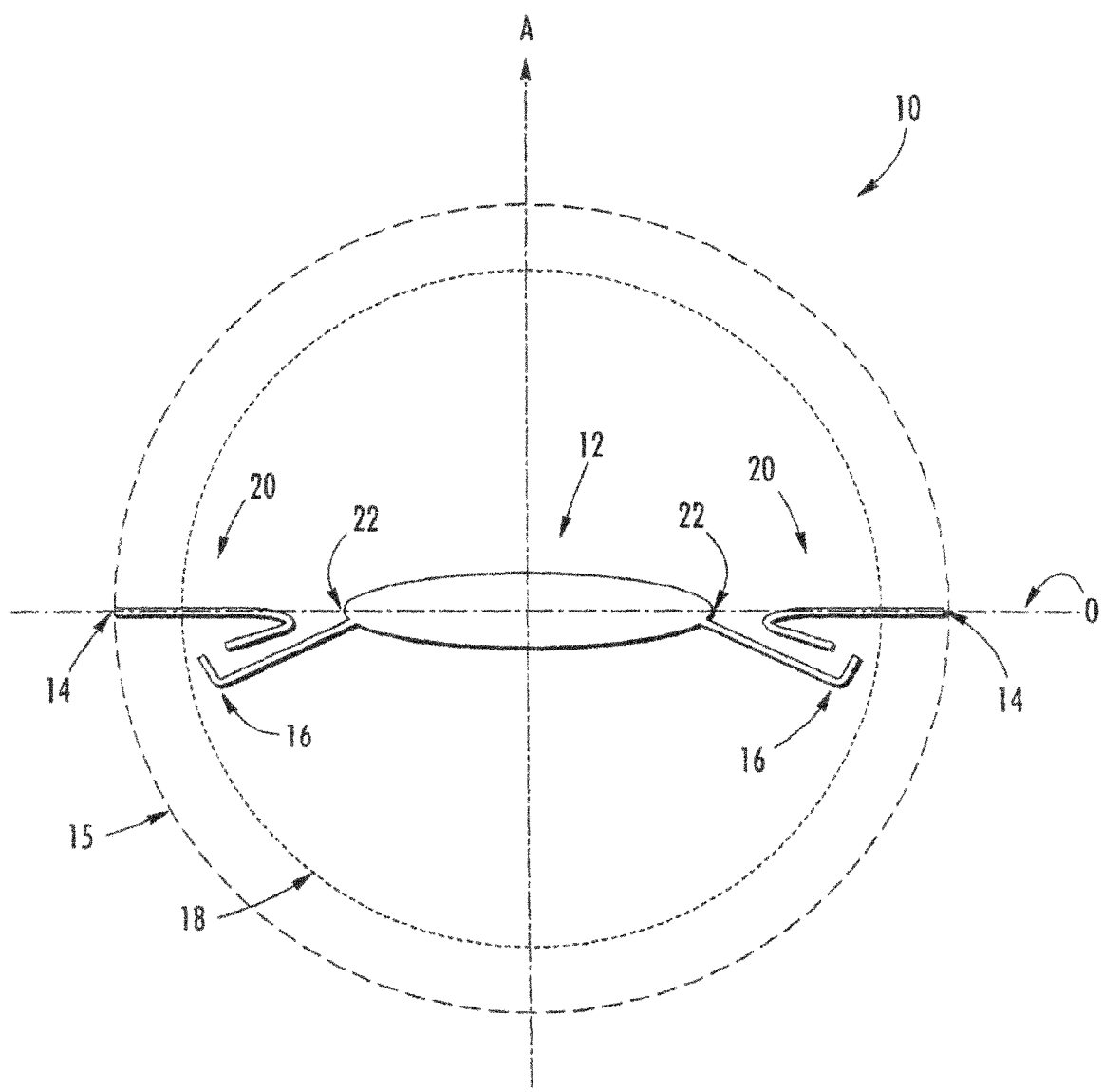
FIG. 5 is a side section view of intraocular implant 10.

FIG. 5 shows a side view of implant 10. Optic portion 12 has a circumferential edge 22 which lies substantially within optic plane O. As shown, centering anchor points 14 also lie within optic plane O. Note, however, in some embodiments the centering anchor points may be in an angled position (i.e. anterior or posterior to) optic plane O. Fixation anchor portions 16 are located posterior to optic plane O. Each haptic 20 extends at an angle to optic plane O from circumferential edge 22 to a first fixation anchor portion 20. The haptic 20 continues on, angling toward the anterior of the eye to connect to a centering anchor portion 16 located in the optic plane O. From centering anchor portion 16, the haptic 20 continues, angling towards the posterior of the eye to connect to a second fixation anchor portion (not shown in the side view) located posterior to optic plane O. Finally, from the second fixation portion 16, the haptic 20 extends back to circumferential edge 22 of optic portion 12, completing a closed loop.

Figure 6A:
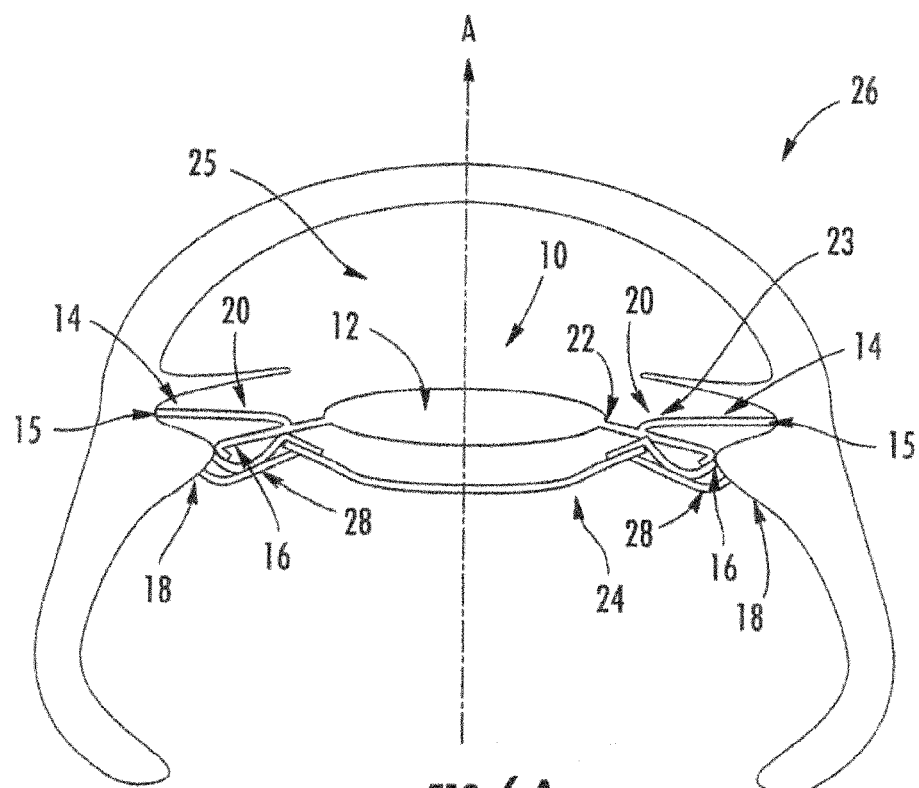
FIG. 6*a* is a side view of implant 10 positioned within an aphakic human eye.
Figure 6B:
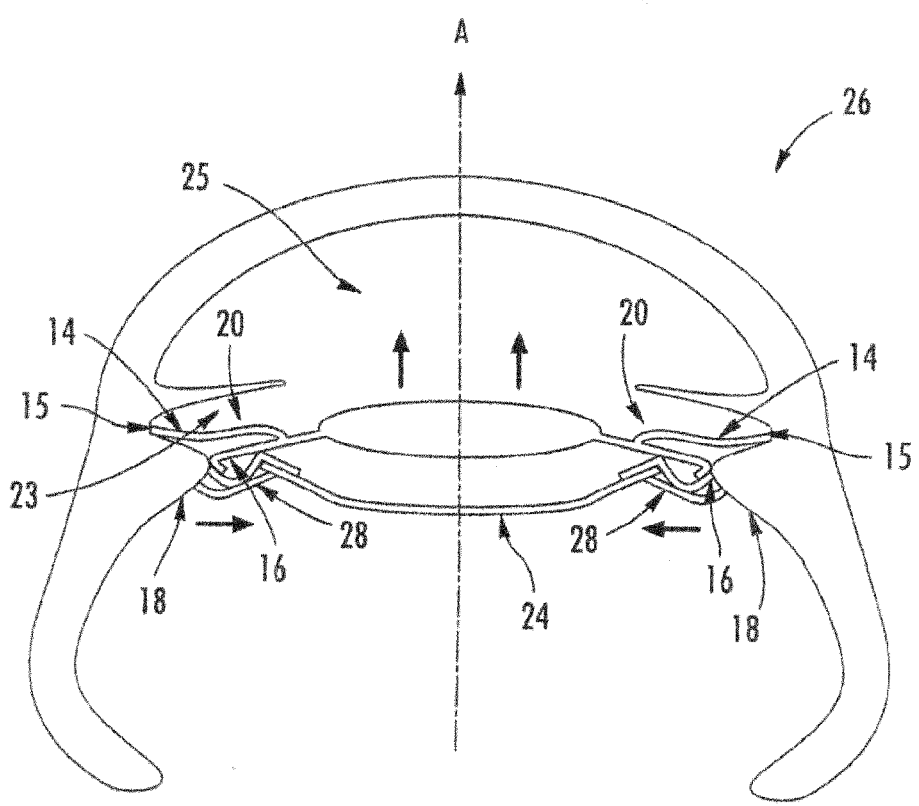
FIG. 6*b* is a side view of implant 10 positioned within an aphakic human eye showing accommodation in response to ciliary muscle relaxation.

FIGS. 6a and 6b show a side view of implant 10 positioned within the posterior chamber 23 outside of capsular bag remnant 24 of aphakic human eye 26. Fixation anchor portions 16 extend from the sides of haptics 20 facing the anterior of the eye 26 and are received by the zonules 28 of the ciliary body/muscle 18. Centering anchor portions 14 are received by the ciliary sulcus 15.

In FIG. 6b, the ciliary muscle 18 has contracted to provide accommodation. The muscle action moves the zonules 28 and attached fixation anchor portions 16 inward as indicated by the small arrows. Haptics 20 transfer this motion to optic portion 12, moving it forward along vision axis toward anterior chamber 25, as indicated by the small arrows. The motion of optic portion 12 adjusts the optical properties of the eye (e.g. refractive power) thereby providing accommodation. Similarly, relaxation of ciliary body/muscle 18 will move optic portion 12 towards the posterior of eye 26. Accordingly, accommodation between near vision and far vision is provided using natural muscular action.

During the muscle action and accommodation motion of optic portion 12, centering anchor portions 16 anchored in the sulcus remain substantially stationary. Haptics 20 connect the substantially fixed centering anchor portions to optic portion 12, and thereby act to maintain the coaxial alignment of optic portion 12 with vision axis A. Accordingly, accommodation is provided while maintaining good centration (e.g. coaxial alignment along vision axis A) of optic portion 12 of implant 10.

Figure 7A:
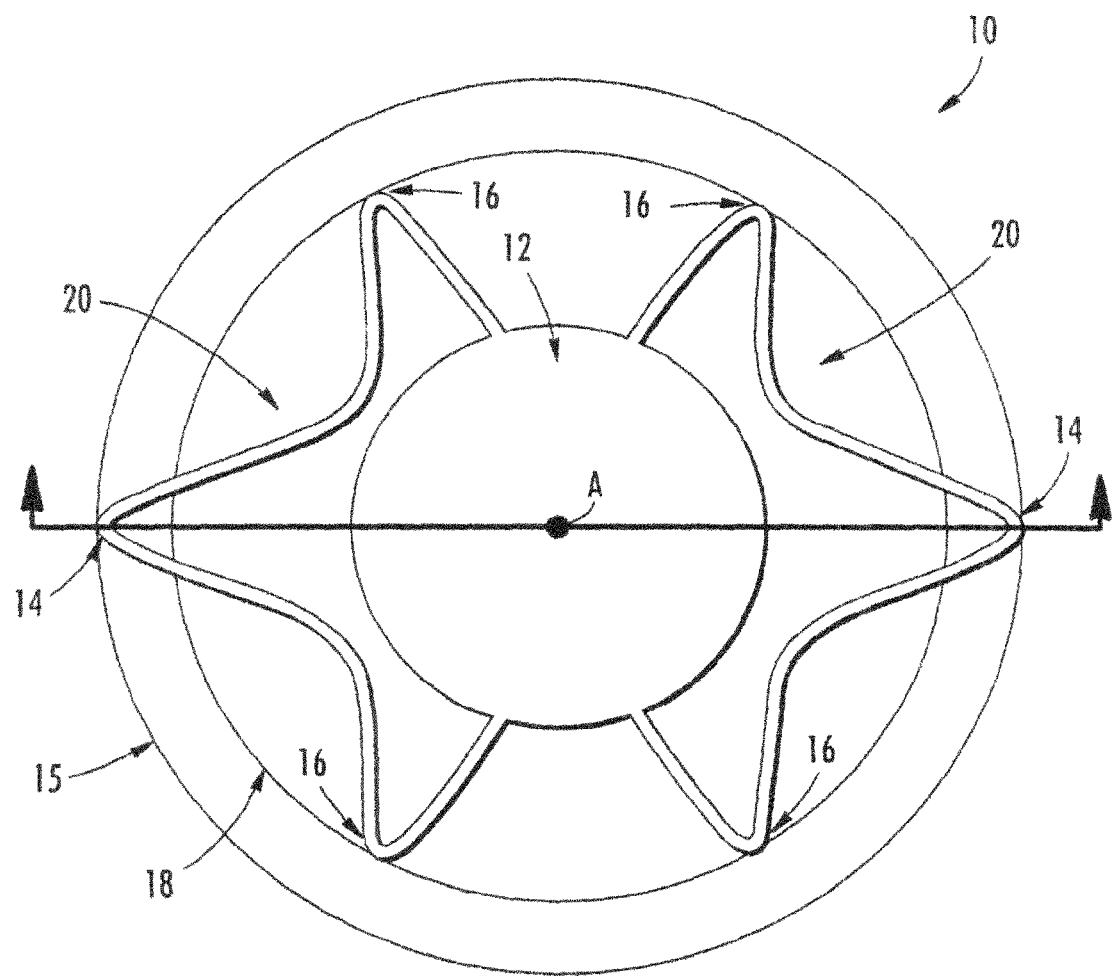
FIG. 7*a* shows a front view of implant 10.
Figure 7B:
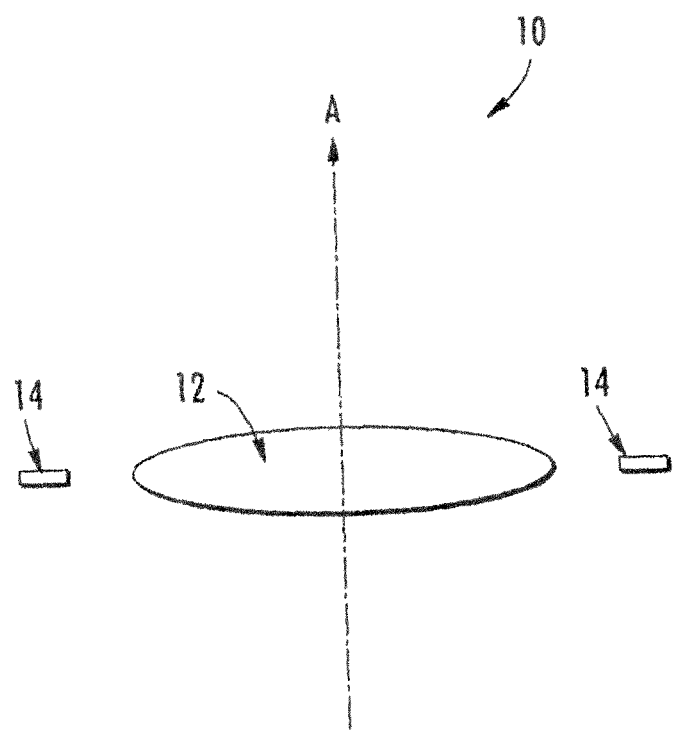
FIG. 7*b* shows a cross section of implant 10.
Figure 7C:
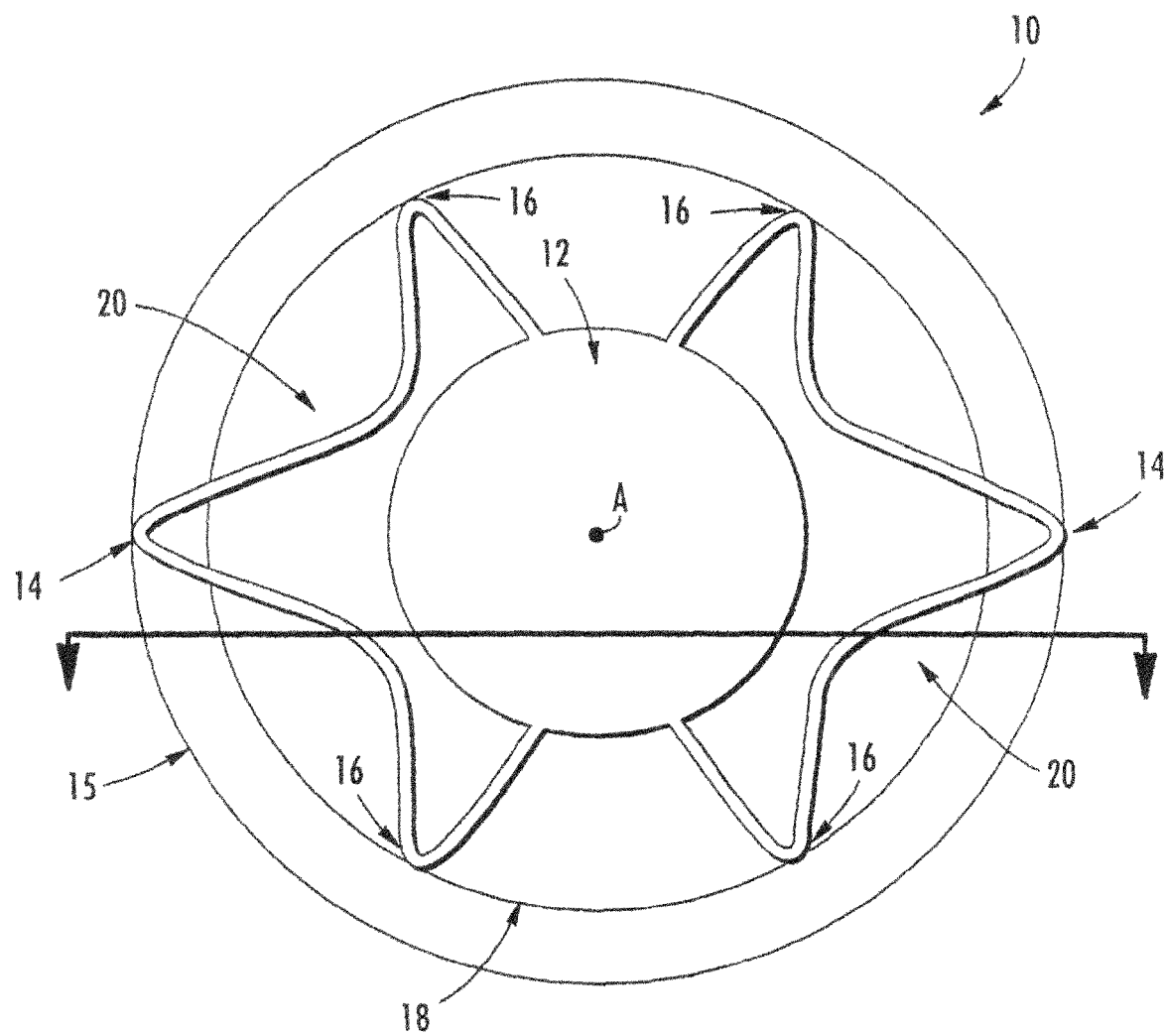
FIG. 7*c* shows a front view of implant 10.

FIGS. 7a, 7c, 7e, 7g, and 7i show front views of implant 10; FIGS. 7b, 7d, 7f, 7h, and 7j show accompanying side view cross sections of implant 10. The orientations of the sections are indicated in the figures by thick black lines through the respective front views. FIG. 7b shows a cross section through the centering anchor portions 14. As shown, the centering anchor portions 14 are in the same plane as edge 22 of optic portion 12. As noted above, however, in some embodiments, the position of the centering anchor portions may be angled, e.g., by a few degrees.

Figure 7D:
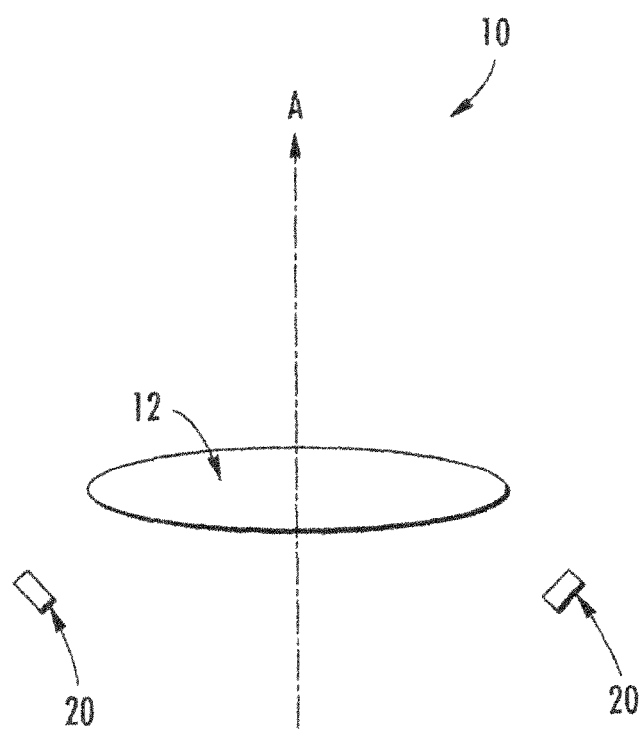
FIG. 7*d* shows a cross section of implant 10.
Figure 7E:
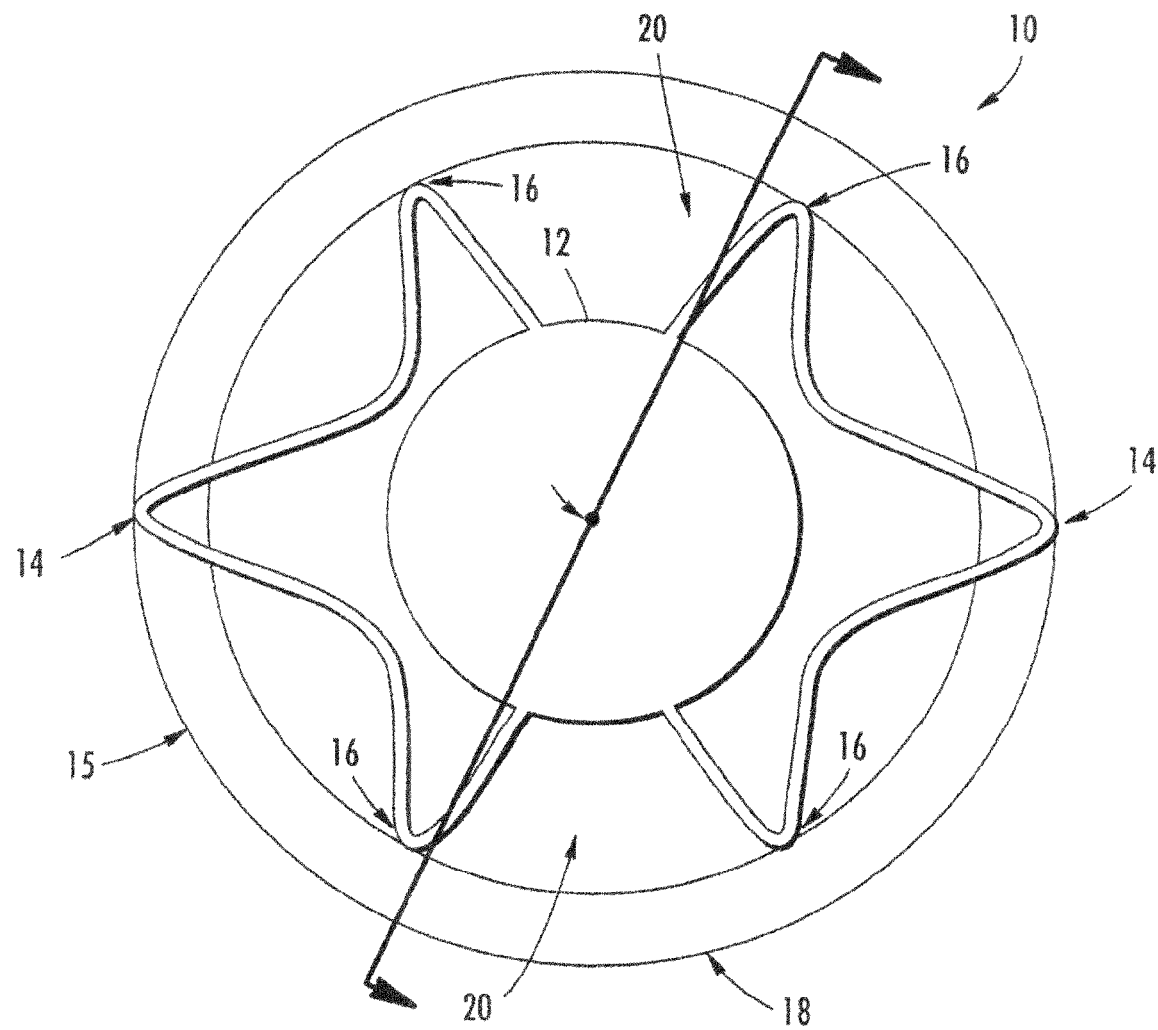
FIG. 7*e* shows a front view of implant 10.

FIG. 7d shows a cross section of implant 10 intersecting haptics 20 at portions along the haptic loop midway between a fixation anchor portion 16 and a centering anchor portion 14. At this point the haptics 20 are posterior to optic portion 12, as fixation anchor portions 16 are posterior to and the accompanying centering anchor portions 14, which, as noted above, in the same plane as the optic portion 12.

Figure 7F:
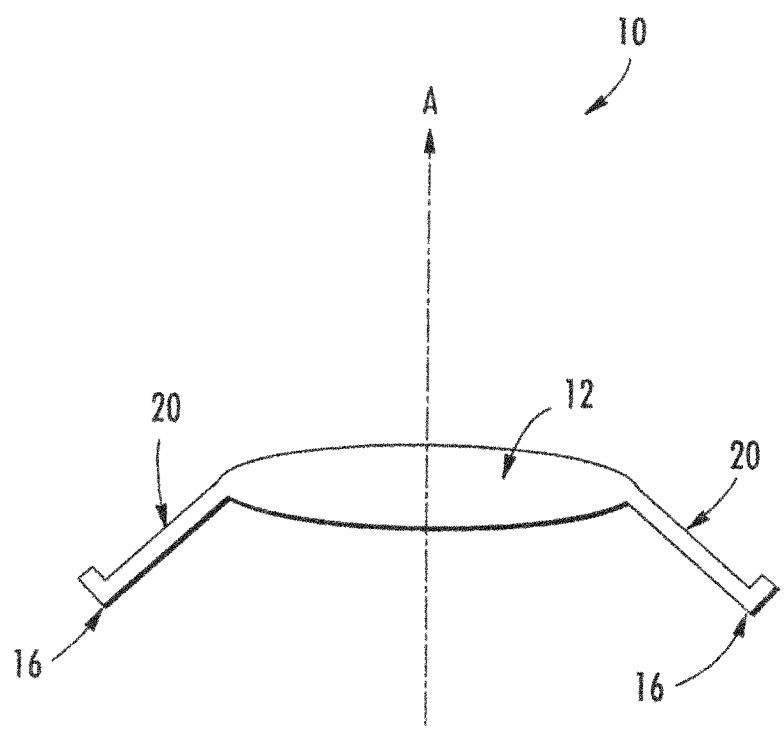
FIG. 7*f* shows a cross section of implant 10.
Figure 7G:
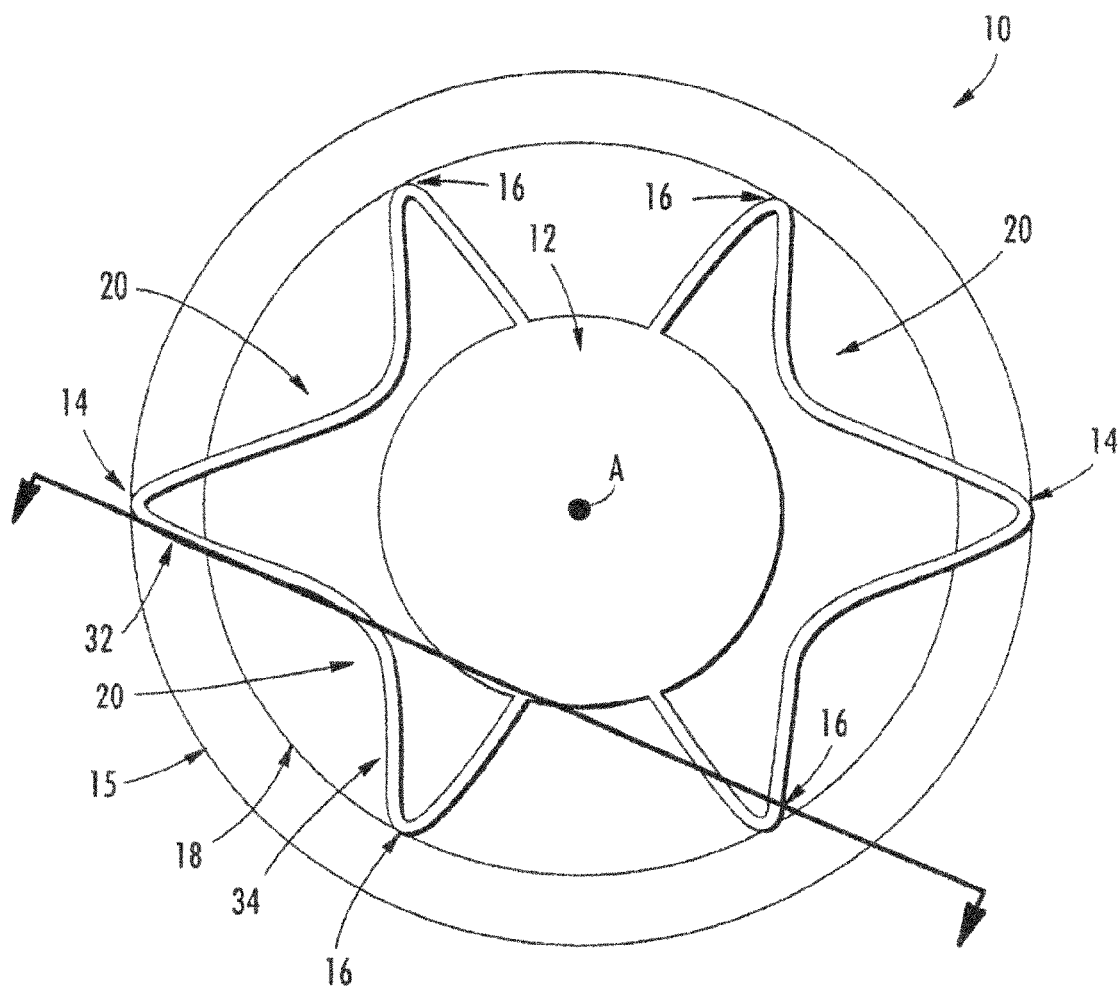
FIG. 7g shows a front view of implant 10.

FIG. 7f shows a cross section of implant 10 through the haptics 20 along the portions of the haptics 20 extending from edge 22 of optic portion 12 to fixation anchor portions 16. As noted above, these portions of the haptics 20 angle posterior to the optic portion 12. Fixation anchor portions 16 are formed as angled tips of the haptic.

Figure 7H:
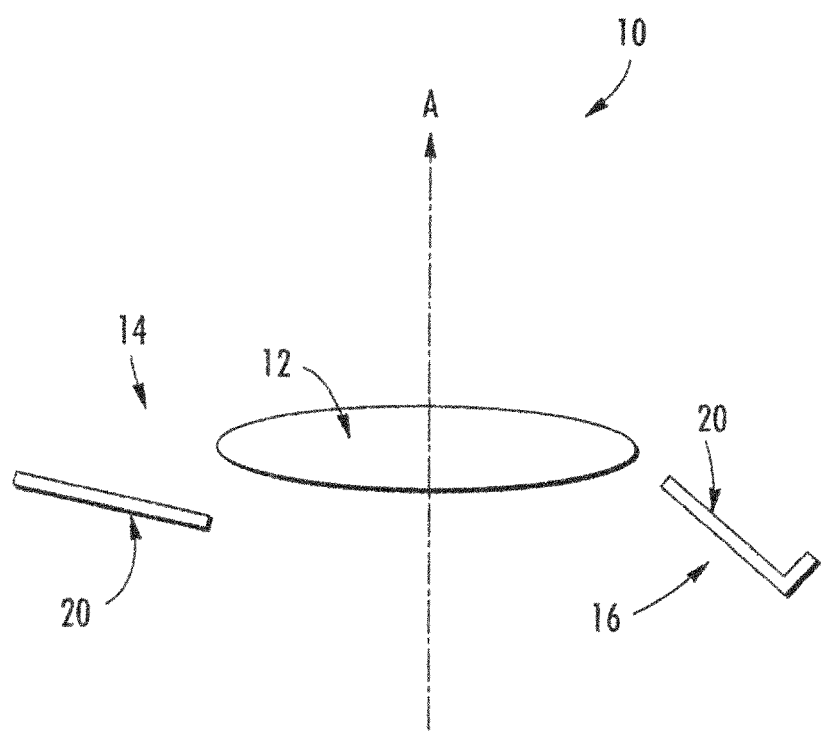
FIG. 7h shows a cross section of implant 10.
Figure 71:
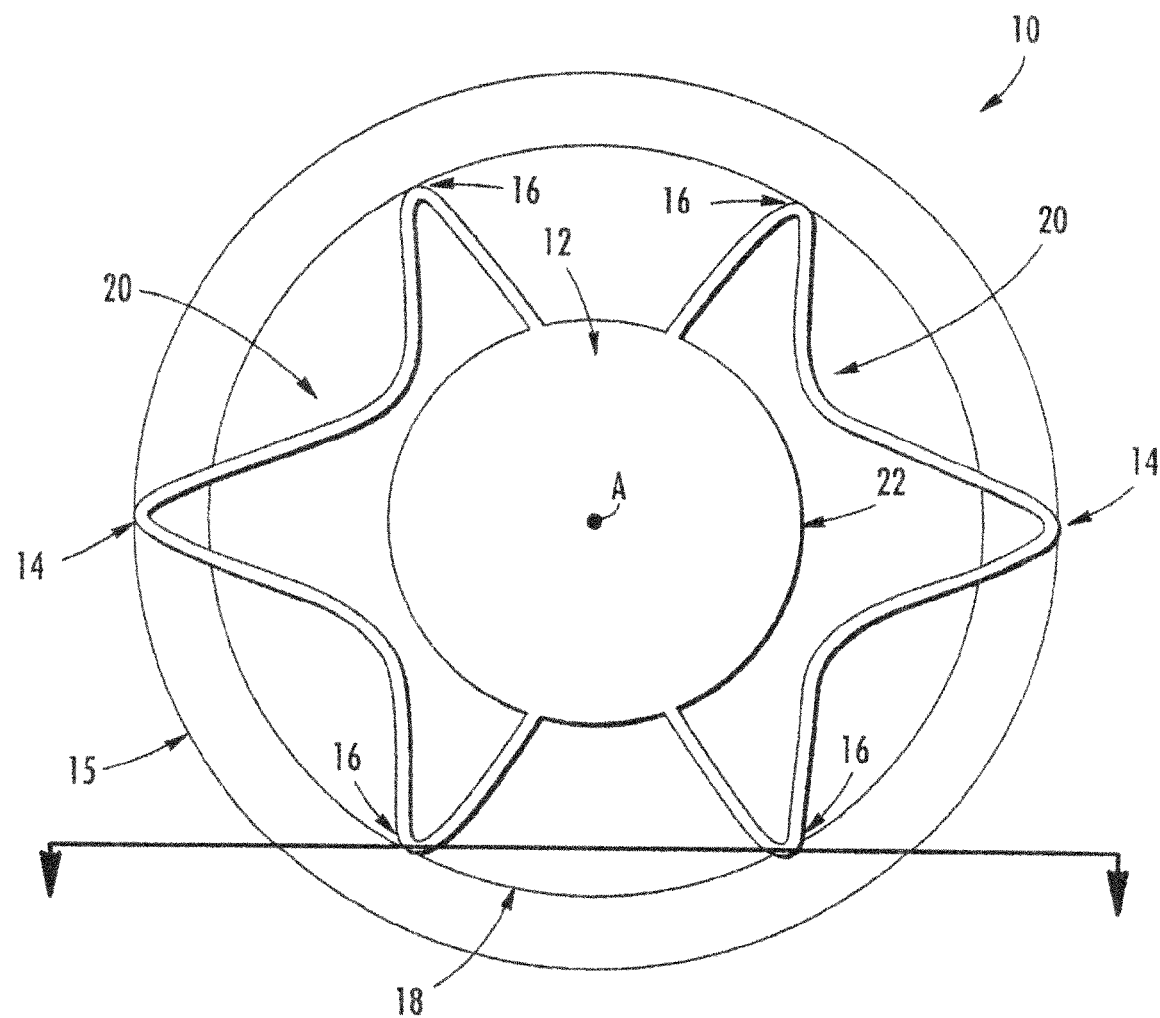

FIG. 7h shows a cross section of implant 10 through a portion 32 of a first haptic 20 connecting a centering anchor portion 14 and a fixation anchor portion 16, and through a portion 34 of a second haptic 20 extending from edge 22 of optic portion to fixation anchor portion 16. Portion 32 of the first haptic 20 angles towards the anterior to connect to the centering anchor portion 14 located in the plane of the optic portion 12. Portion 34 of the second haptic 20 angles towards the posterior to connect to fixation anchor portion 16. Again, the fixation anchor portion 16 is shown formed as an angled tip of haptic 20.

Figure 7J:
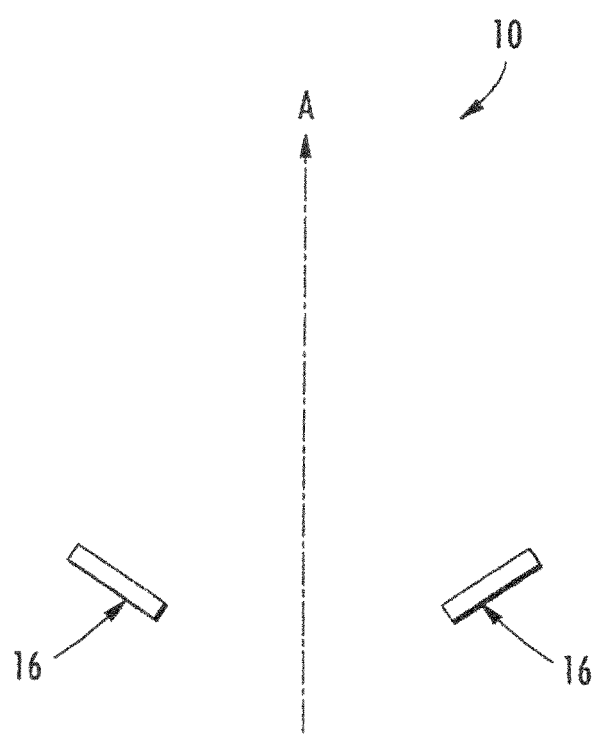
FIG. 7j shows a cross section of implant 10.

FIG. 7j shows a cross section of implant 10 through the fixation anchor portions 16. Fixation anchor portions 16 are shown formed as angled tips of haptics 20, with a serrated surface on the posterior sides of the haptics 20 at the tips for gripping the zonules 28 of the ciliary body/muscle 18.

Figure 8A:
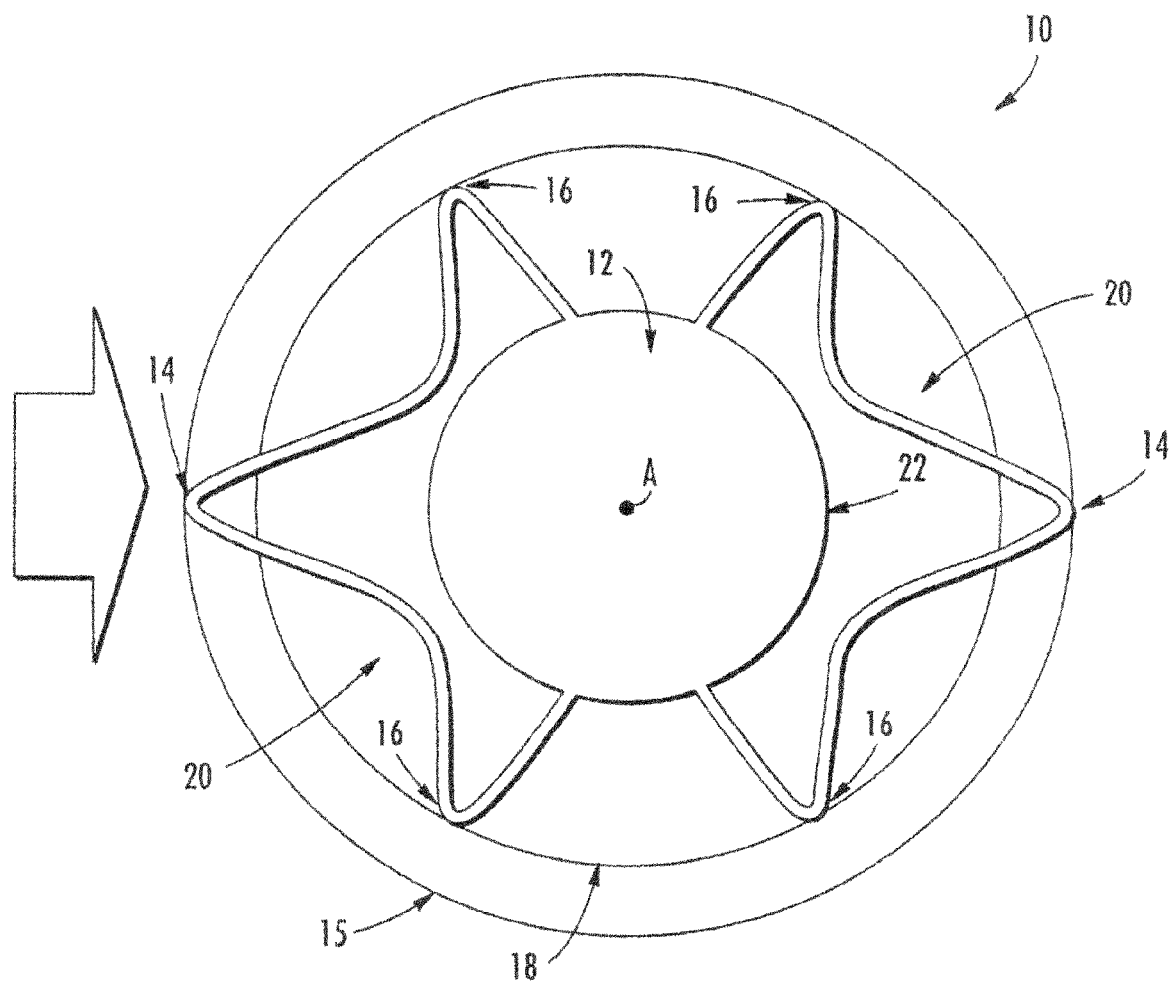
FIG. 8a shows a front view of implant 10.
Figure 8B:
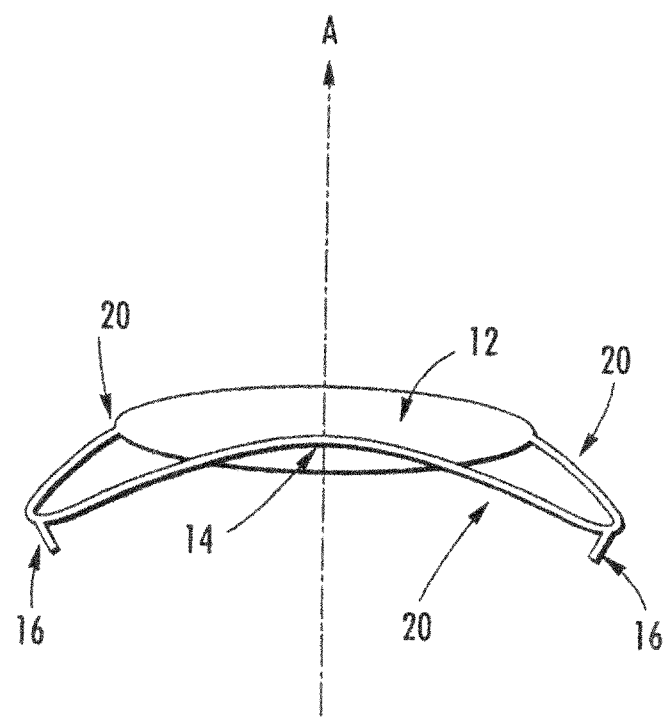
FIG. 8b shows a side elevation of implant 10.

FIG. 8a shows a front view of implant 10; FIG. 8b shows an accompanying side elevation of implant 10 viewed from the direction indicated by the broad arrow. Again, the portion of the haptics 20 extending from edge 22 to fixation anchor portions 16 angle posterior to the optic. The portions connecting the fixation anchor portions 16 to the centering anchor portions 14 come anterior until they are roughly in the plane of optic portion 12, where the haptics 20 extend out to reach past the ciliary body/muscle 18 to the sulcus 15.

Figure 9:
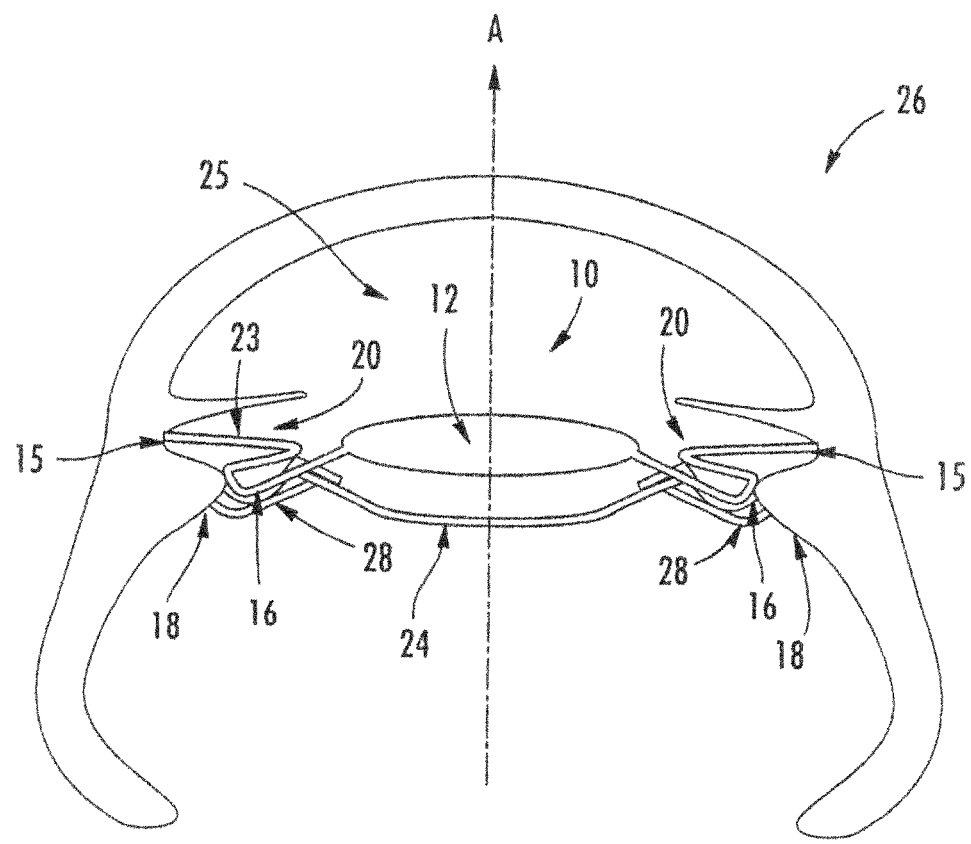
FIG. 9 shows a side view of implant 10 positioned within an aphakic human eye.

Although on exemplary embodiment is shown above, it is to be understood that various modifications and alternative embodiments are within the scope of this disclosure. For example, as shown in FIGS. 5a and 5b, implant 10 is positioned outside of capsular bag 24. However, in some embodiments, the implant may be positioned inside of the bag 24. FIG. 9 shows a modification of implant 10 in which fixation anchoring portions 16 are located on the sides of the haptics 20 facing the posterior of the eye.

Figure 10:
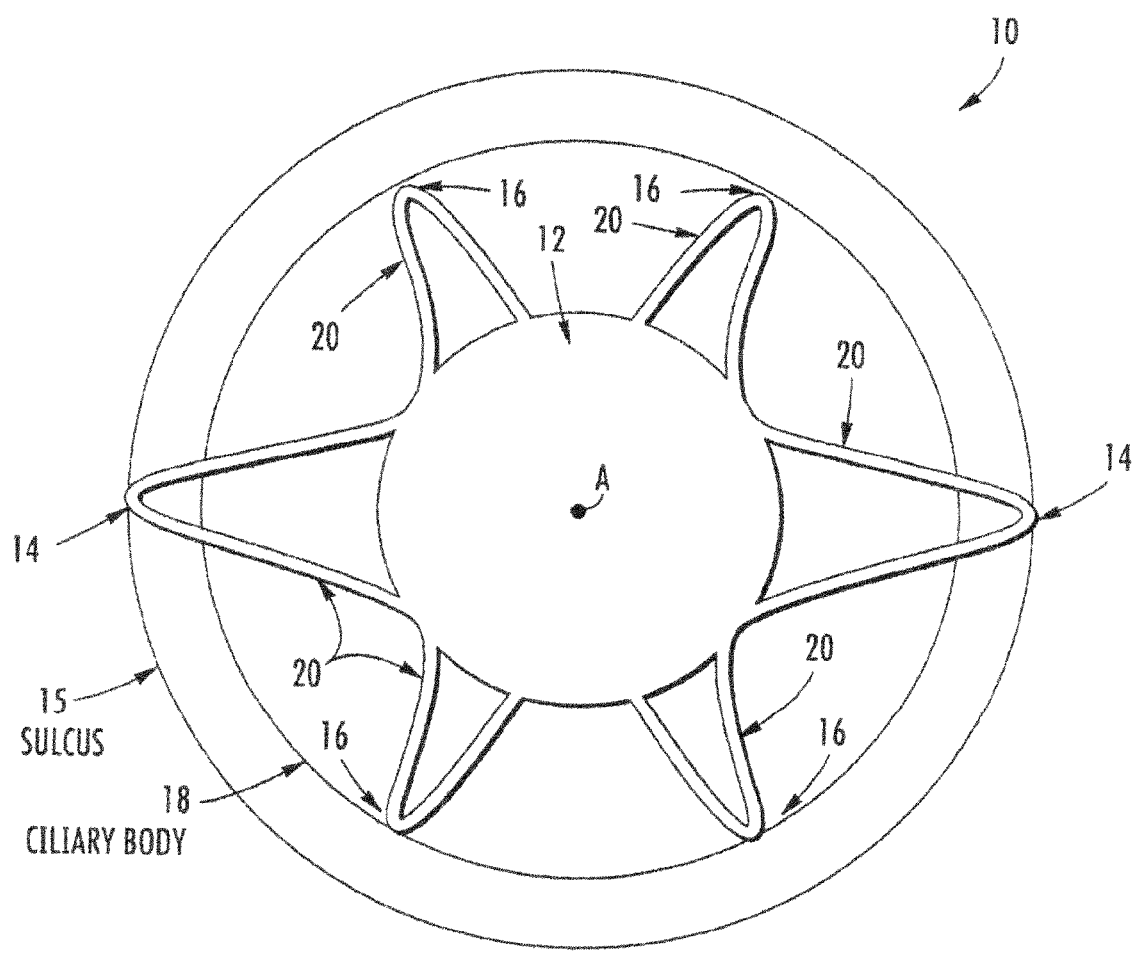
FIG. 10 shows a front view of implant 10 with an exemplary haptic configuration.

FIGS. 10 through 16b show embodiments of implant 10 featuring various haptic configurations. For example, FIG. 10 shows a front view of an embodiment of implant 10 featuring two centering anchor portions 14 received by the sulcus 15 and four fixation anchor portions 16 received by the ciliary body muscle 18 (or zonules 28, not shown). Each of the anchor portions 14, 16 is connected to optic portion 12 by a corresponding closed loop haptic 20. The haptics 20 corresponding to centering anchor portions 14 extend out to the sulcus 15, and may lie in the plane of optic portion 12, or be angled by, for example, a few degrees to the anterior or posterior. The haptics 20 corresponding to fixation anchor portions 16 extend posterior at an angle to the plane of optic portion 12 toward the ciliary body 18. As in the embodiment above, muscle action of the ciliary body 18 is transferred by the fixation anchor portions 16 and corresponding haptics 20 to move optic portion 12 along vision axis A, thereby providing accommodation. During accommodation, centering anchor portions remain substantially fixed within the sulcus 15, and corresponding haptics 20 hold optic portion 12 in coaxial alignment with vision axis A.

Figure 11:
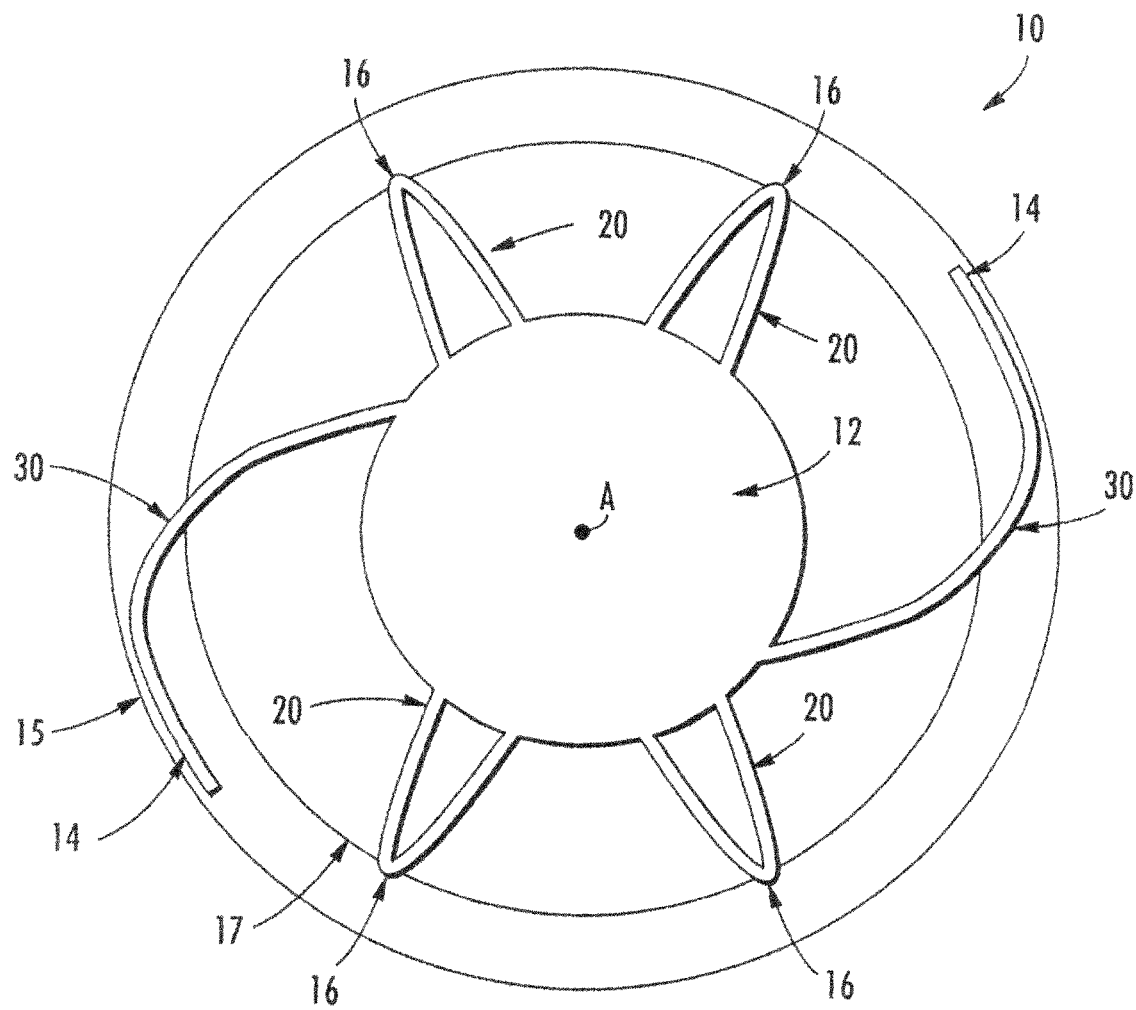
FIG. 11 shows a front view of implant 10 with an exemplary haptic configuration.

FIG. 11 shows a front view of an embodiment of implant 10 featuring two centering anchor portions 14 received by the sulcus 15 and four fixation anchor portions 16 received by the ciliary body 18. As in the embodiment shown in FIG. 10, each of the fixation anchor portions 16 is connected to optic portion 12 by a corresponding open loop haptic 20. However, centering anchor portions 14 are each connected to optic portion 12 with open loop haptic 30 (e.g. a haptic with a curved portion which extends from and curves back towards, but does not reattach to optic portion 12). Again, the fixation anchor portions 16 and corresponding haptics 20 transfer ciliary muscle motion to provide accommodation, while centering anchor portions 14 and corresponding haptics 30 maintain the desired alignment of optic portion 12.

Figure 12A:
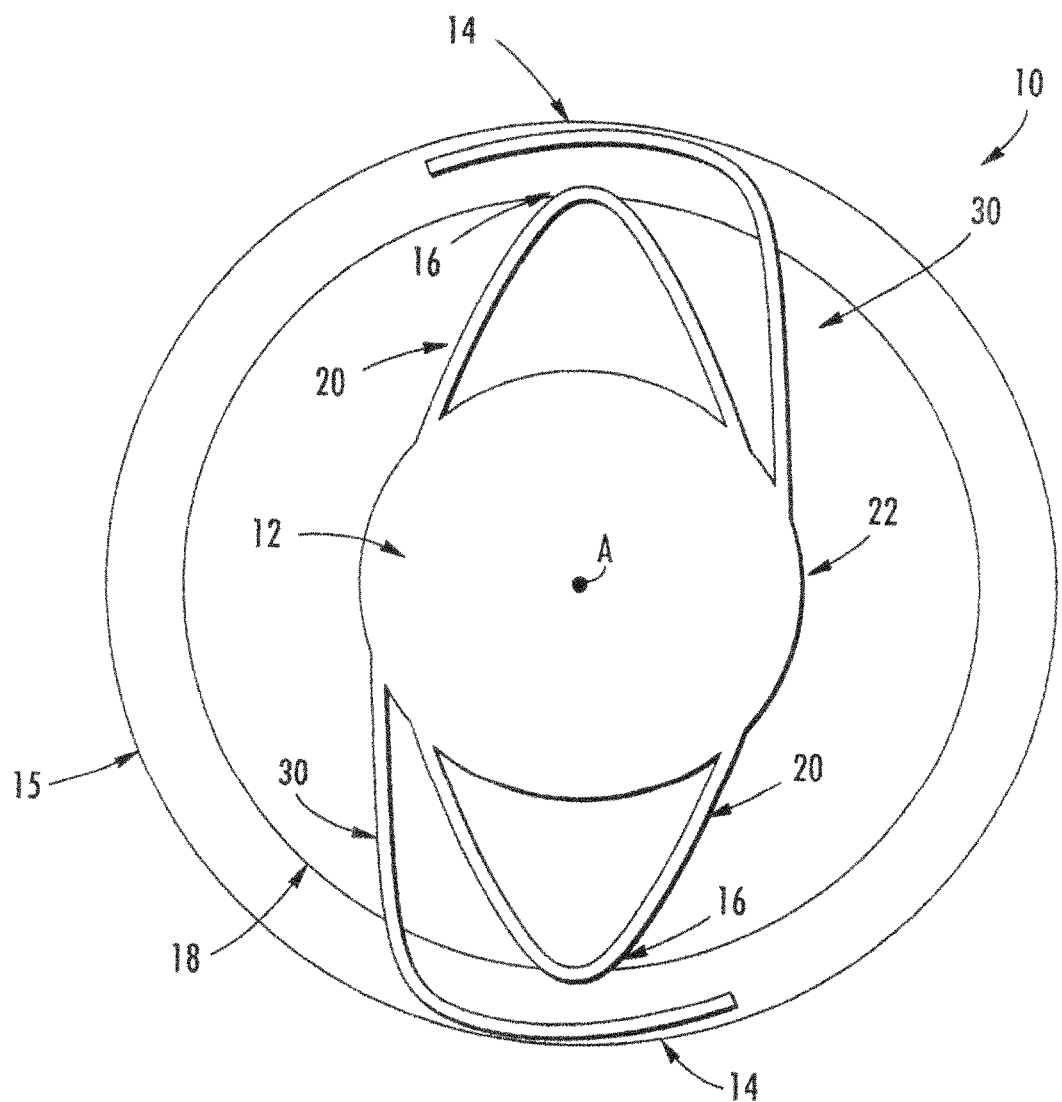
FIG. 12a shows a front view of implant 10 with an exemplary haptic configuration.

FIG. 12a shows a front view of an embodiment of implant 10 featuring two centering anchor portions 14 received by the sulcus 15 and two fixation anchor portions 16 received by the ciliary body 18. The centering anchor portions 14 are connected to optic portion 12 with open loop type haptics 30 extending in opposing directions from the circumferential edge 22 of optic portion 12. Similarly, the fixation anchor portions 16 are connected to optic portion 12 with open loop type haptics 30, each open loped haptic 30 extending in from the circumferential edge 22 in substantially the same direction as a corresponding closed loop haptic 20.

Figure 12B:
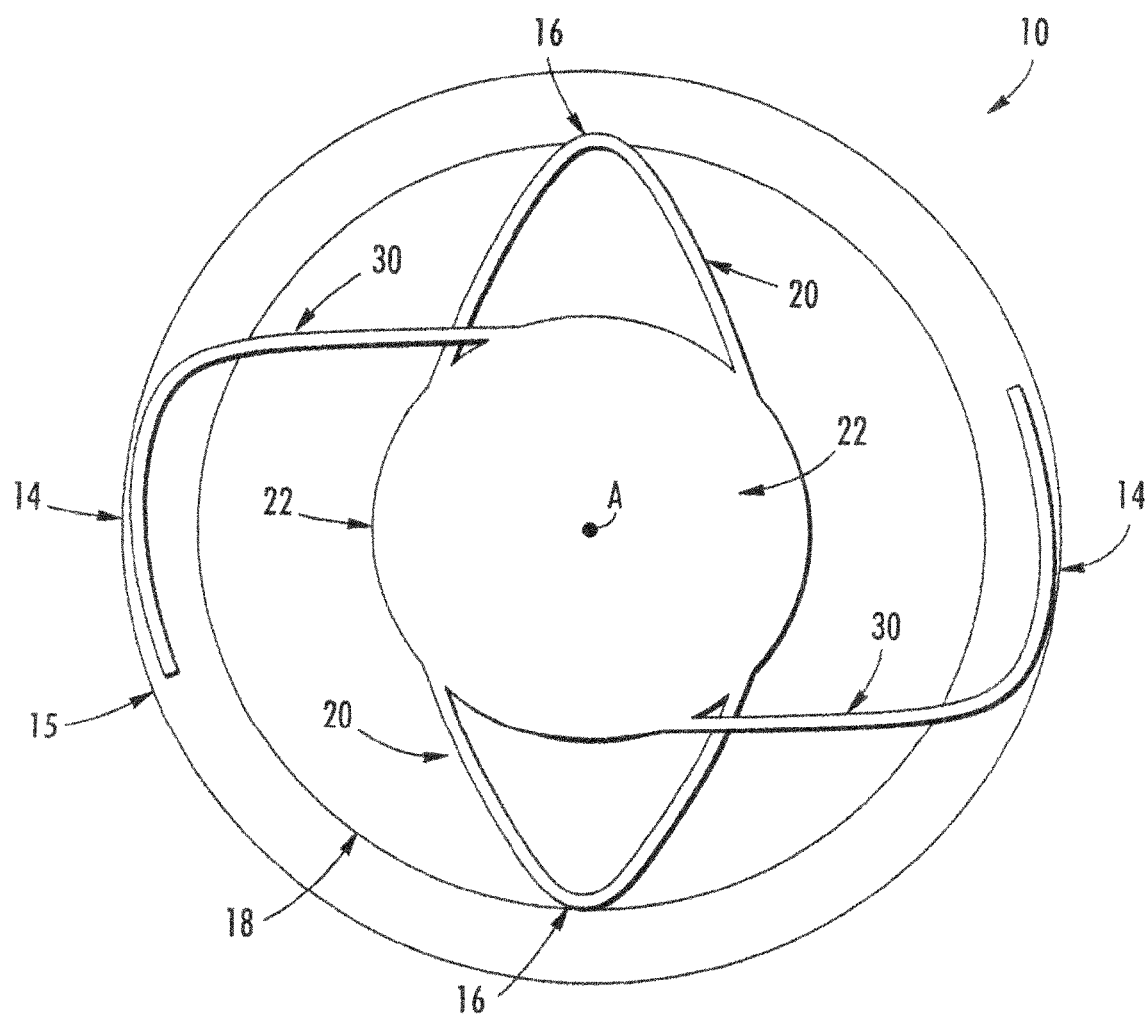

FIG. 12b shows a front view of an embodiment of implant 10 similar to that shown in FIG. 12a, but with the position of centering anchor portions 14 and corresponding open loop haptics 30 rotated by about 90 degrees relative to fixation anchor portions 16 and corresponding close looped haptics 20 (i.e. fixation anchor portions 16 are located at roughly twelve o'clock and six o'clock in the plane of optic portion 12, while centering anchor portions 14 are located at roughly three o'clock and nine o'clock). It is to be understood that, in various embodiments, the relative position of these components may form any arbitrary angle.

Figure 13A:
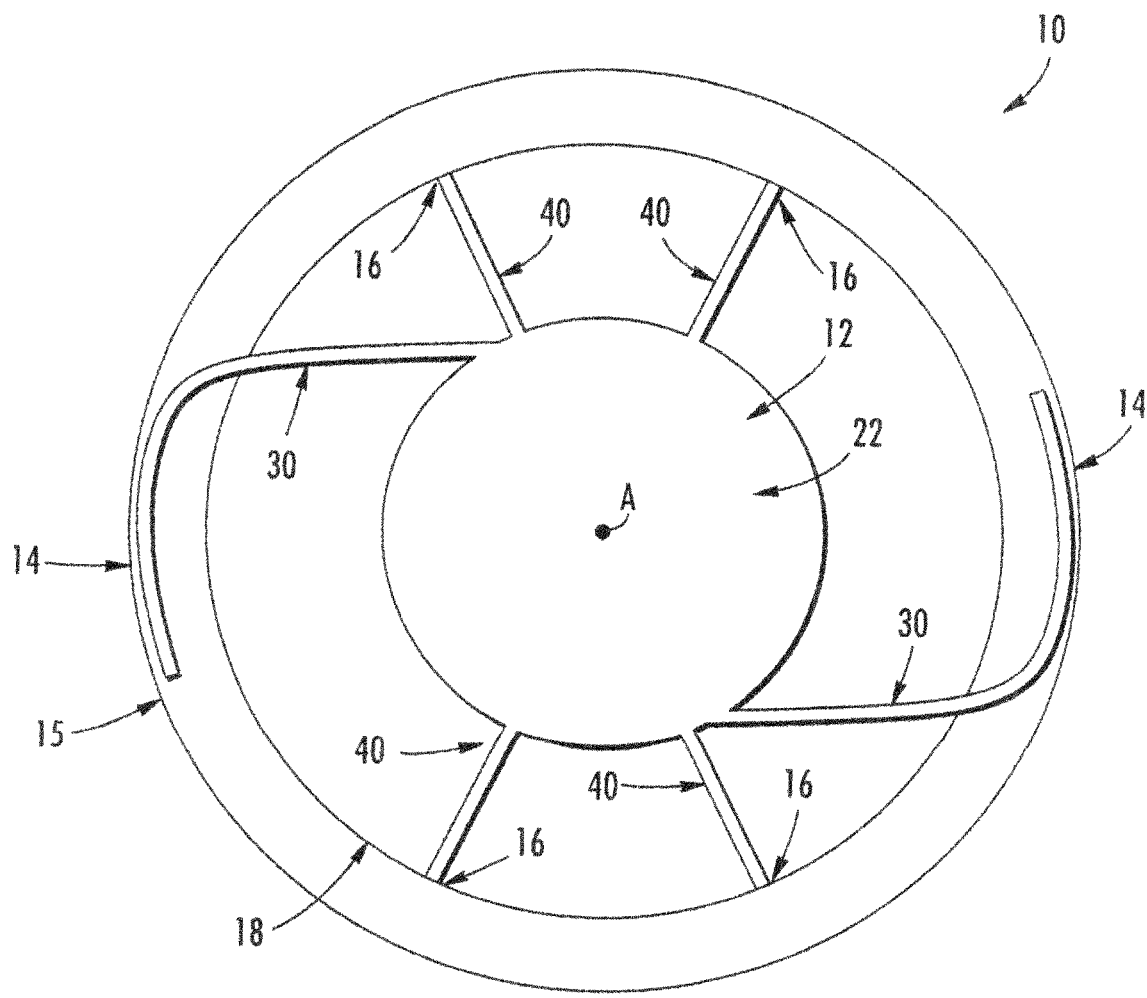
FIG. 13a shows a front view of implant 10 with an exemplary haptic configuration.
Figure 13B:
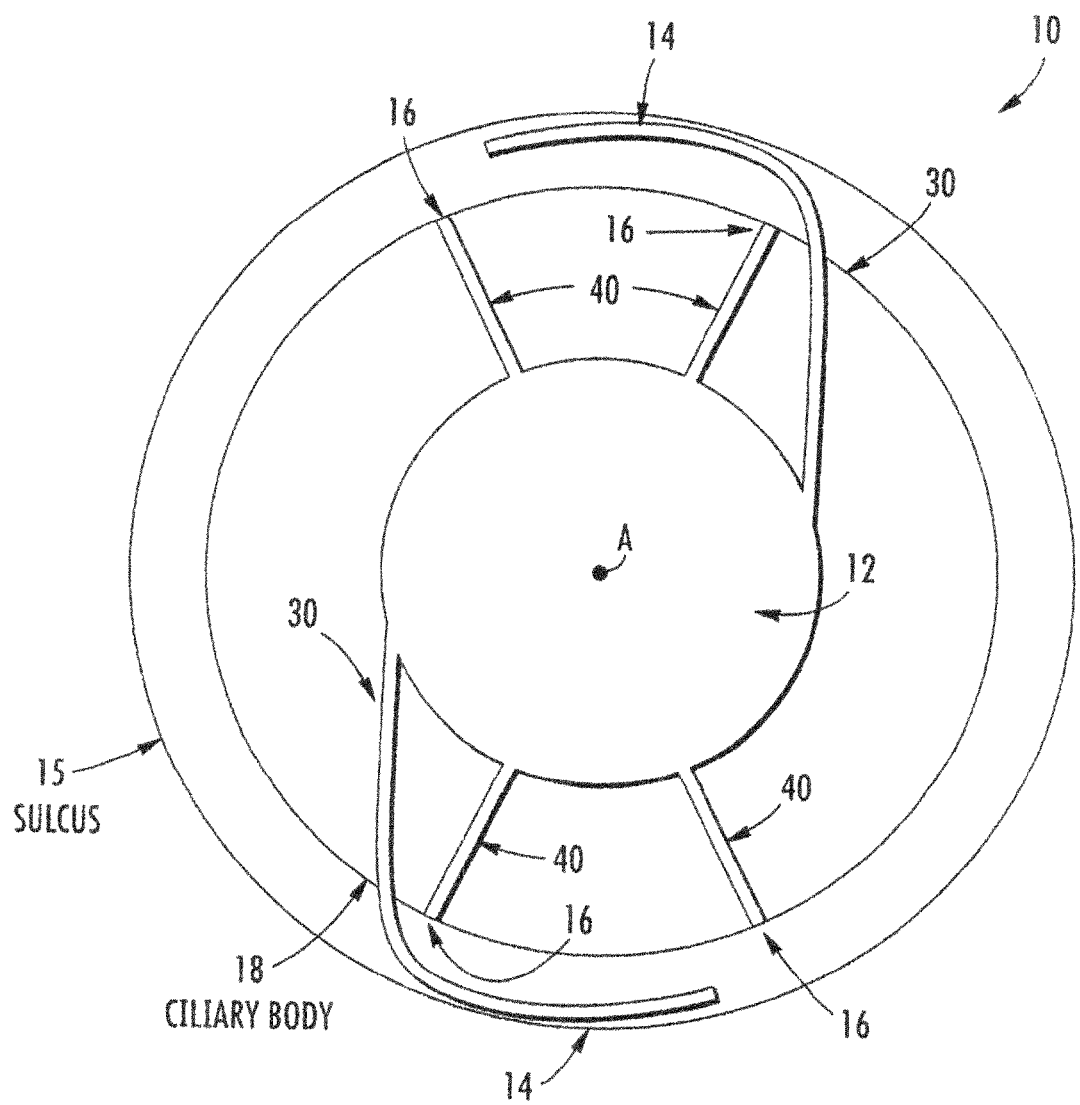

FIG. 13 a shows a front view of an embodiment of implant 10 featuring two centering anchor portions 14 received by the sulcus 15 and four fixation anchor portions 16 received by the ciliary body 18. The centering anchor portions 14 are connected to optic portion 12 by open loop type haptics 30 extending from circumferential edge 22. The fixation anchor portions 16 are each connected to optic portion 12 with corresponding straight type haptic 40 (i.e. a haptic extending in a substantially straight line from optic portion to the fixation anchor portion). In some embodiments, one or more of the straight type haptics 40 may extend to the posterior at an angle to the plane of optic portion 12. As shown in FIG. 13a the centering anchor portions 14 are located at roughly three and nine o'clock in the plane of optic portion 12. FIG. 13b shows an embodiment where the centering anchor portions 14 and corresponding open loop type haptics 30 have been rotated by about 90 degrees, such that the centering anchor portions 14 are located at roughly twelve and six o'clock.

Figure 14A:
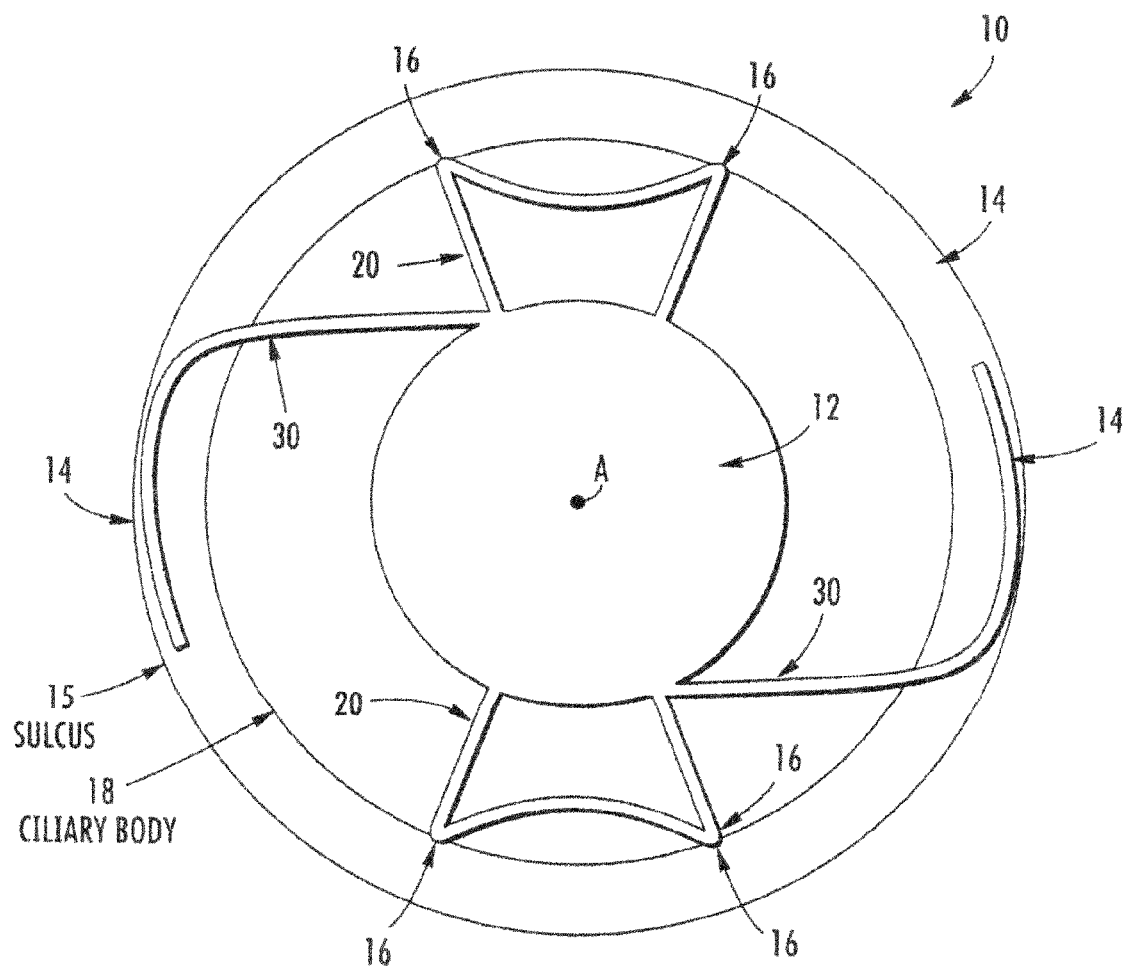
FIG. 14a shows a front view of implant 10 with an exemplary haptic configuration.
Figure 14B:
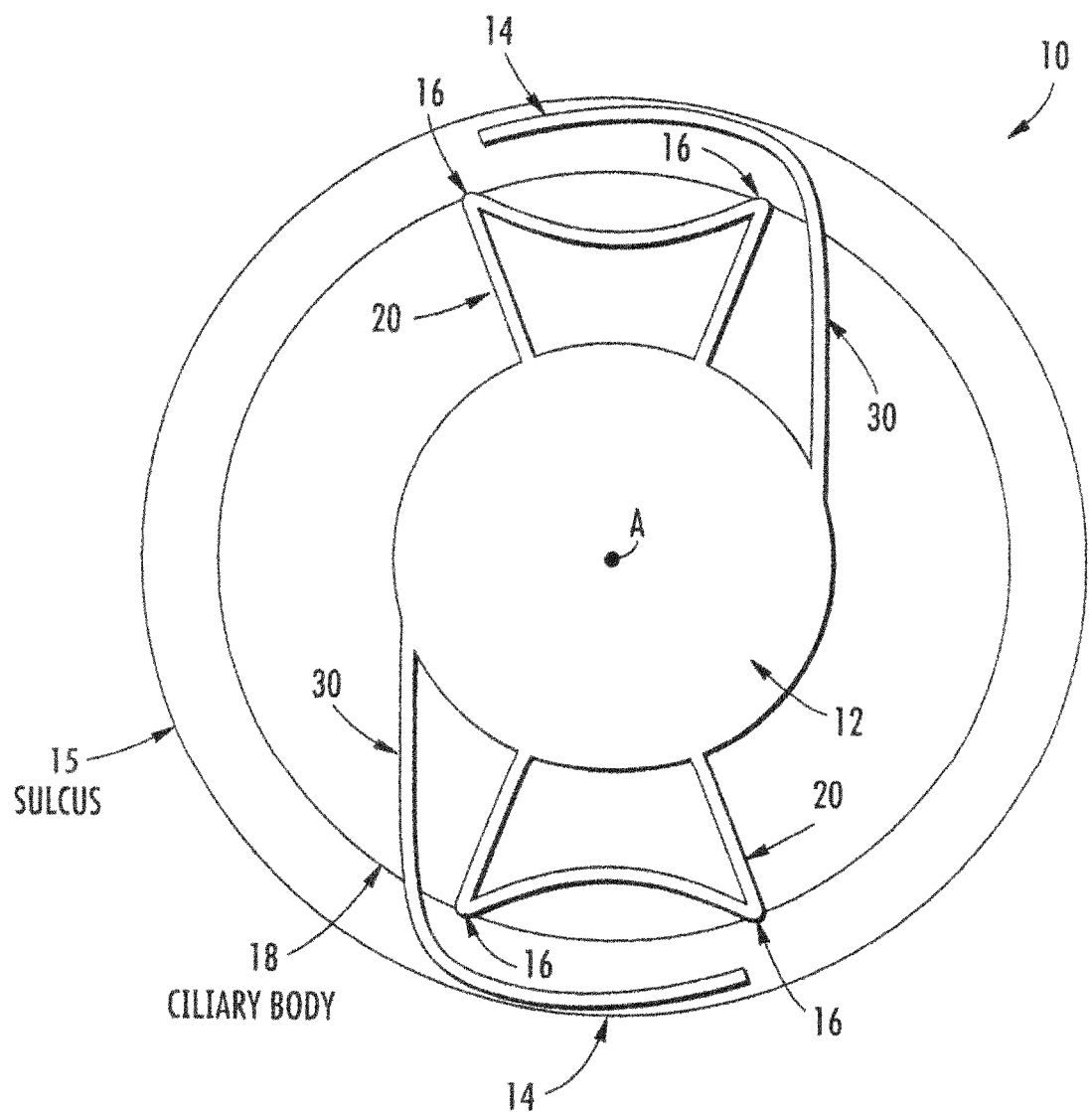

FIG. 14a shows a front view of an embodiment of implant 10 featuring two centering anchor portions 14 received by the sulcus 15 and four fixation anchor portions 16 received by the ciliary body 18. Each of two closed loop type haptics 20 extend from circumferential edge 22 to the ciliary body 18 and connect a pair of the fixation anchor portions 16 to optic portion 12. The centering anchor portions 14 are connected to optic portion 12 by open loop type haptics 30 extending from circumferential edge 22 to the sulcus 15. As shown in FIG. 14a the centering anchor portions 14 are located at roughly three and nine o'clock. FIG. 14b shows an embodiment where the centering anchor portions 14 and corresponding open loop type haptics 30 have been rotated by about 90 degrees, such that the centering anchor portions 14 are located at roughly twelve and six o'clock.

Figure 15:
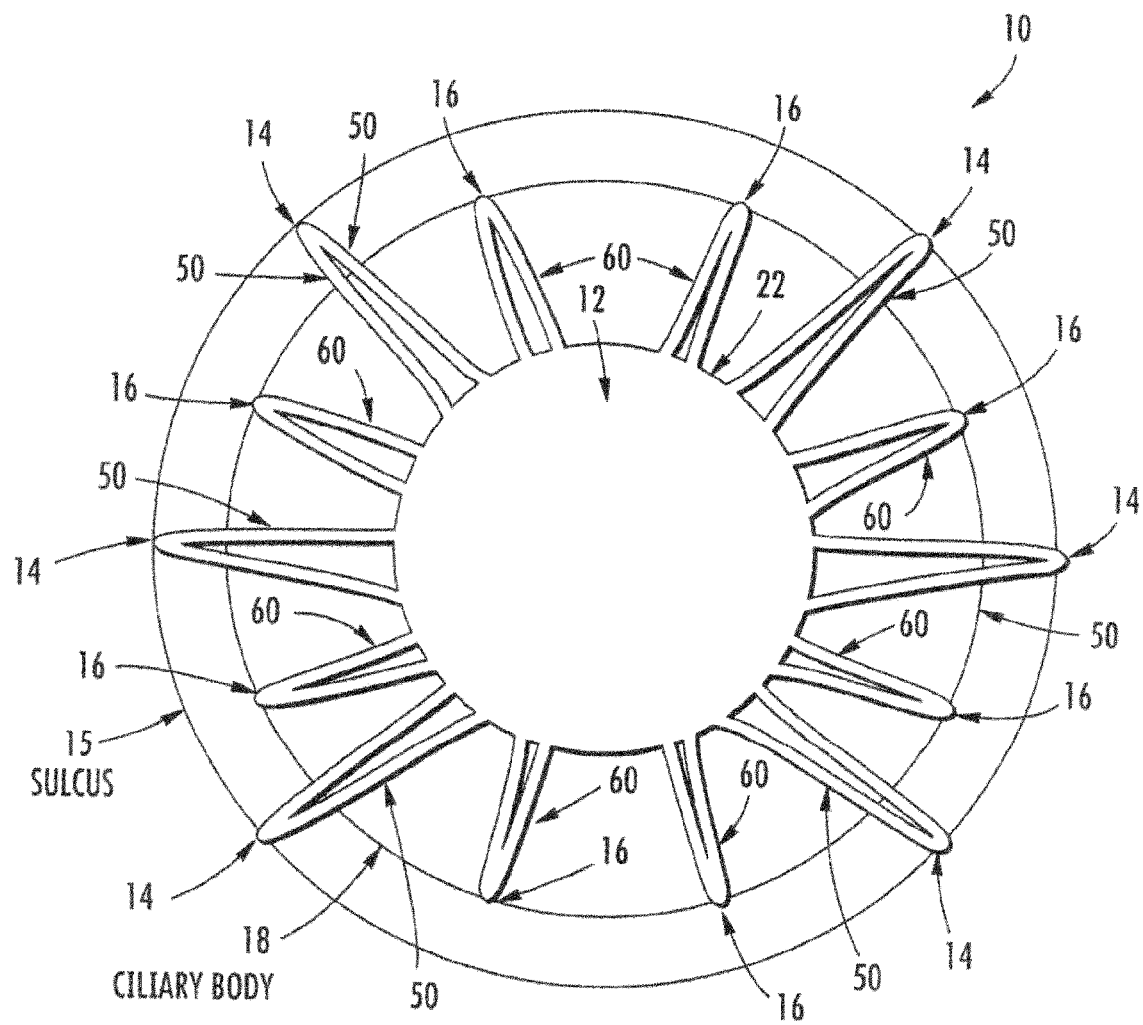
FIG. 15 shows a front view of implant 10 with an exemplary haptic configuration.

FIG. 15 shows a front view of an embodiment of implant 10 featuring six centering anchor portions 14 received by the sulcus 15 and eight fixation anchor portions 16 received by the ciliary body 18. Each centering anchor portion 14 is connected to optic portion 12 by a closed loop type haptic 20 extending from circumferential edge 22 out to the sulcus 15. Each of the fixation anchor portions 16 is connected to optic portion 12 by a closed loop type haptic 20 extending from circumferential edge 22 to ciliary body 16.

Figure 16A:
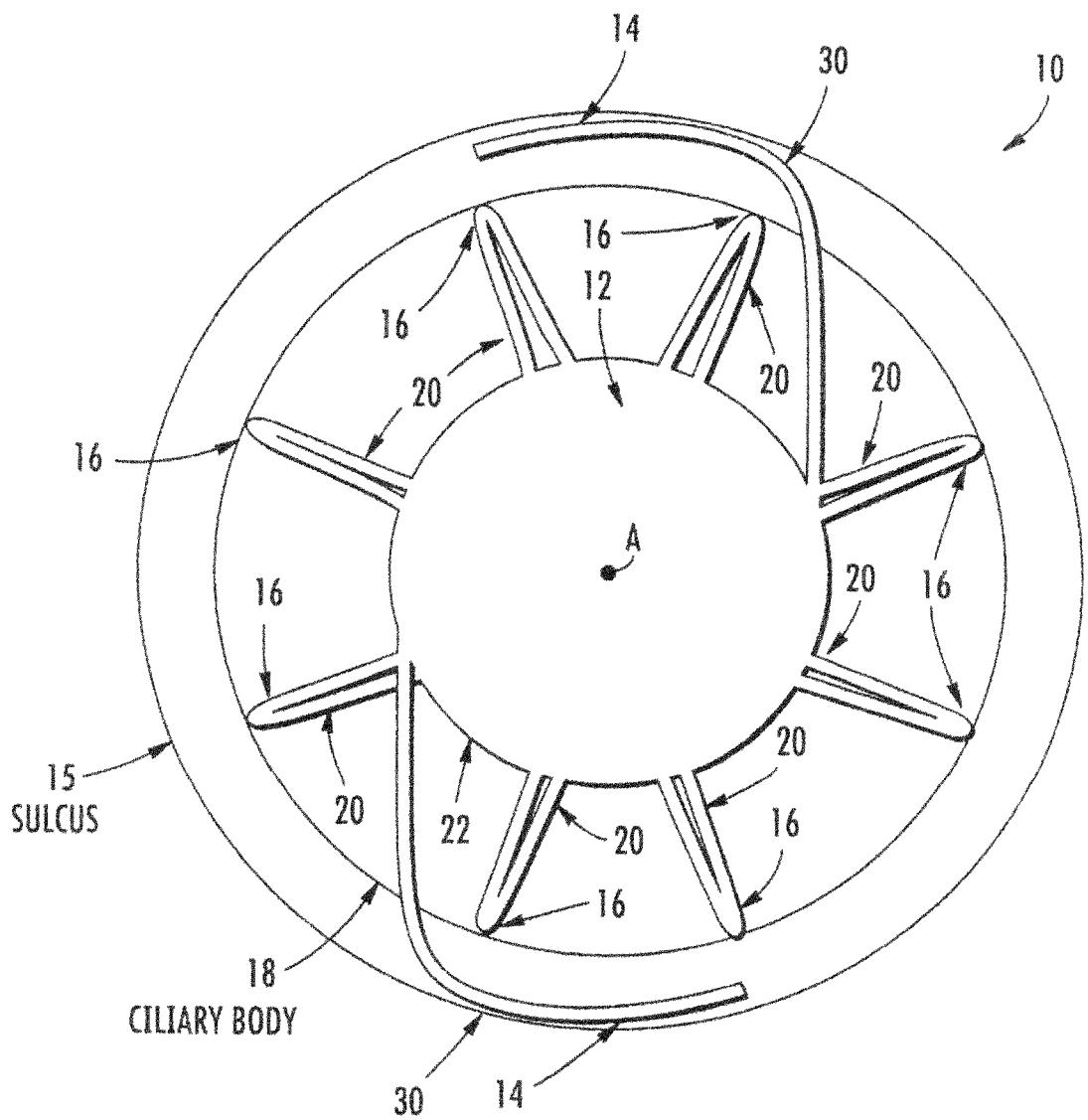
FIG. 16a shows a front view of implant 10 with an exemplary haptic configuration.
Figure 16B:
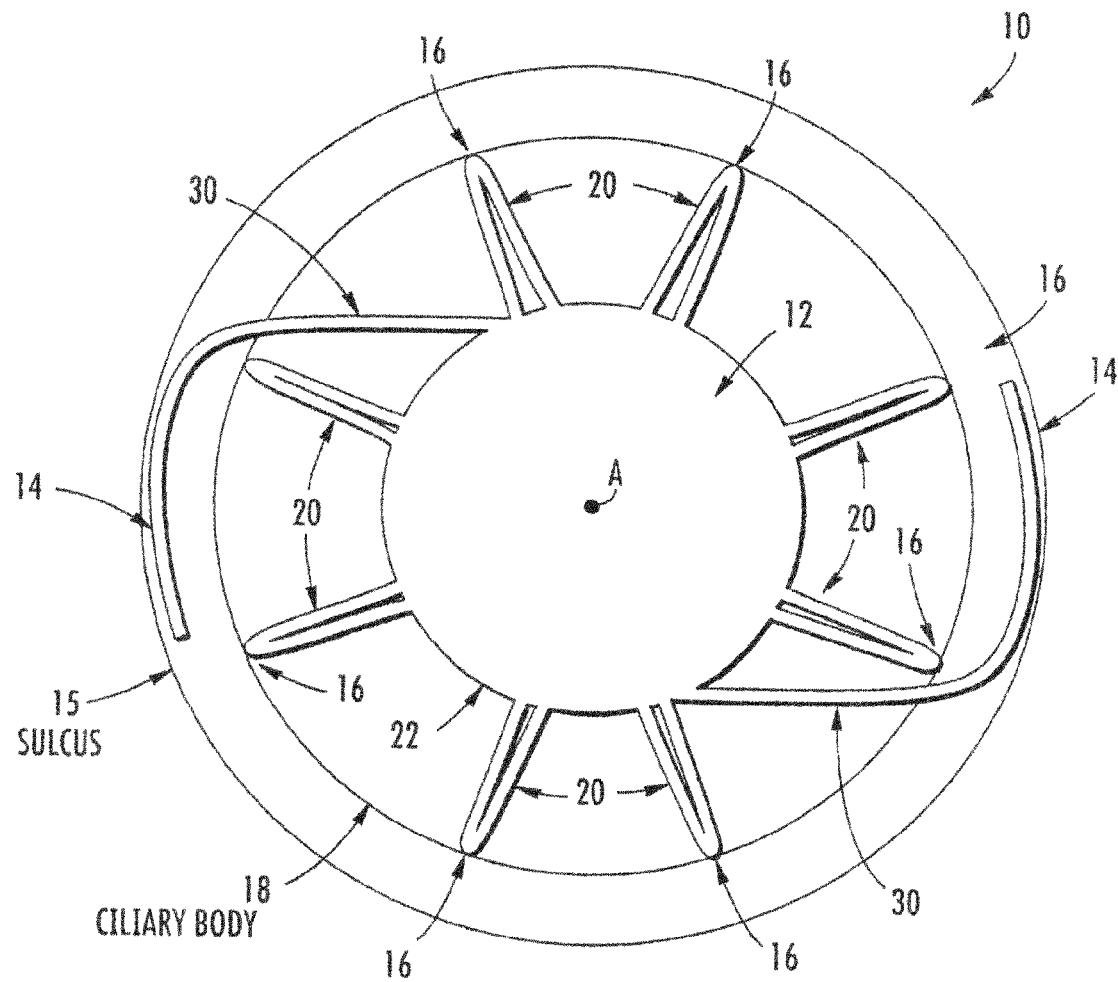

FIG. 16*a* shows a front view of an embodiment of implant 10 featuring two centering anchor portions 14 received by the sulcus 15 and eight fixation anchor portions 16 received by the ciliary body 18. Each fixation anchor portions 16 is connected to optic portion 12 by a closed loop type haptic 20 extending from circumferential edge 22 to ciliary body 16. The centering anchor portions 14 are connected to optic portion 12 by open loop type haptics 30 extending from circumferential edge 22 to the sulcus 15. FIG. 16*b* shows a front view illustrating alternative placement of the embodiment of implant 10 shown in FIG. 16*a*, where the orientation of implant 10 has been rotated 90 degrees with respect to the eye.

Although several examples of haptic systems are presented above, it is to be understood that other suitable configurations may be used. Any number of haptics may be used. Each haptic may connect optic portion 12 to one or more of the centering anchor portions 14 or the fixation anchor portions 16. The connected anchor portions may be integral with the haptic. As shown above, the haptics may be of the open loop type, closed loop type, or straight type. In some embodiments the haptic may be of the paddle type, i.e. solid element (without a central aperture) bounded by a curved, e.g., C-shaped or U-shaped, peripheral edge. The haptics may extend from one or more positions on the periphery of optic portion 12.

Figure 17:
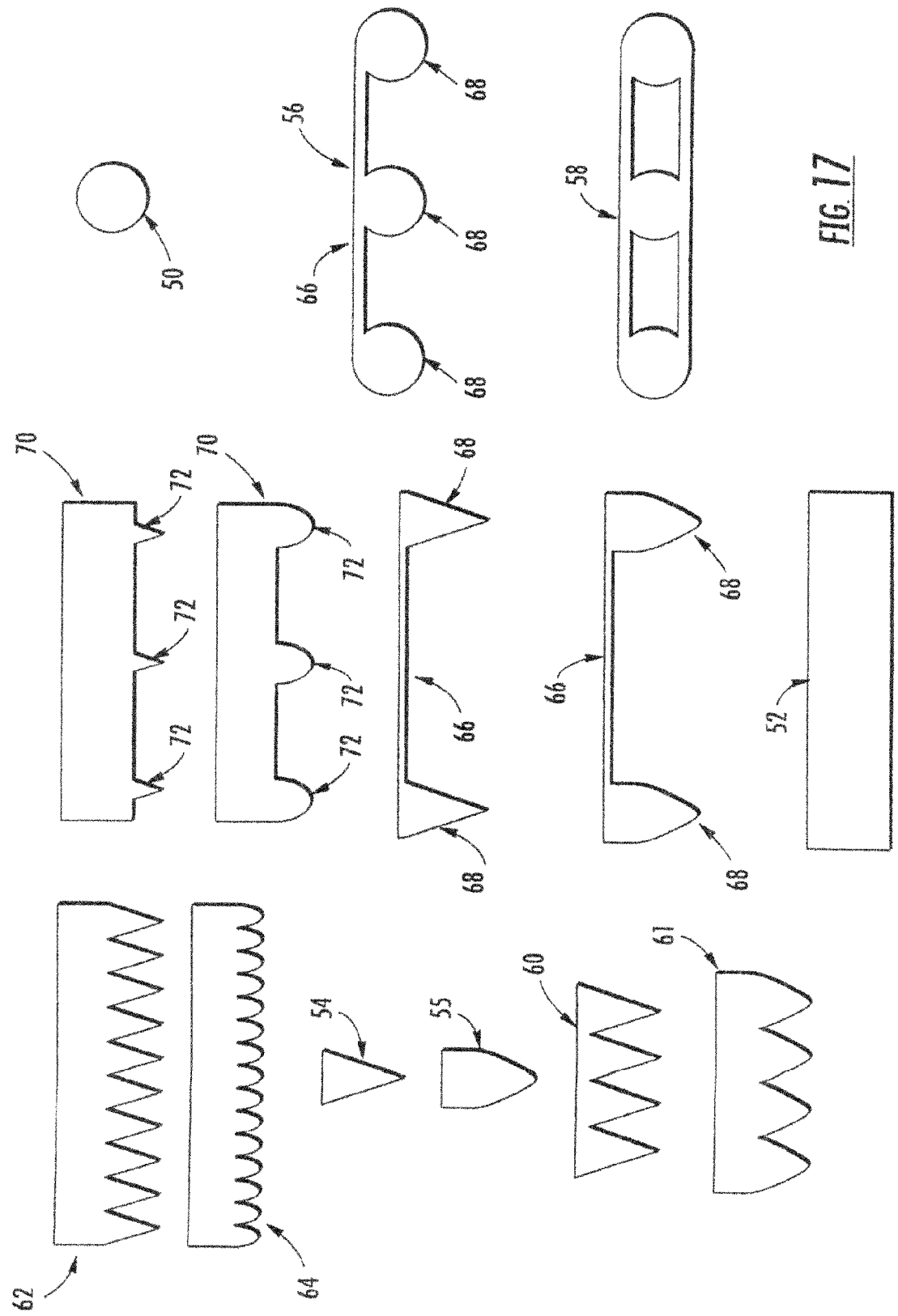
FIG. 17 shows cross sections of various exemplary anchor portions for implant 10.

FIG. 17 shows cross sectional shapes suitable for use as centering anchor portions 14 to be received in the sulcus 15 or fixation anchor portions to be received in the ciliary body/muscle 18 or zonules 28. The cross sectional shapes include a cylinder 50, rectangle 52, wedge 54, modified wedge 55, multiple connected cylinders 56, 58, multiple wedges 60, multiple modified wedges 61, etc. The anchor portion may include a serrated surface 62, scalloped surface 64, etc. The anchor portion may include a relatively thin surface 66 with one or more relatively large protrusions 68 shaped as, for example, wedges, cylinders, modified wedges, etc. The anchor portion may include a relatively thick surface 70 with one or more relatively small protrusions 72 shaped as, for example, wedges, cylinders, modified wedges, etc. In various embodiments, any other configuration which can be received by the relevant portion of the eye may be used.

Figure 18:
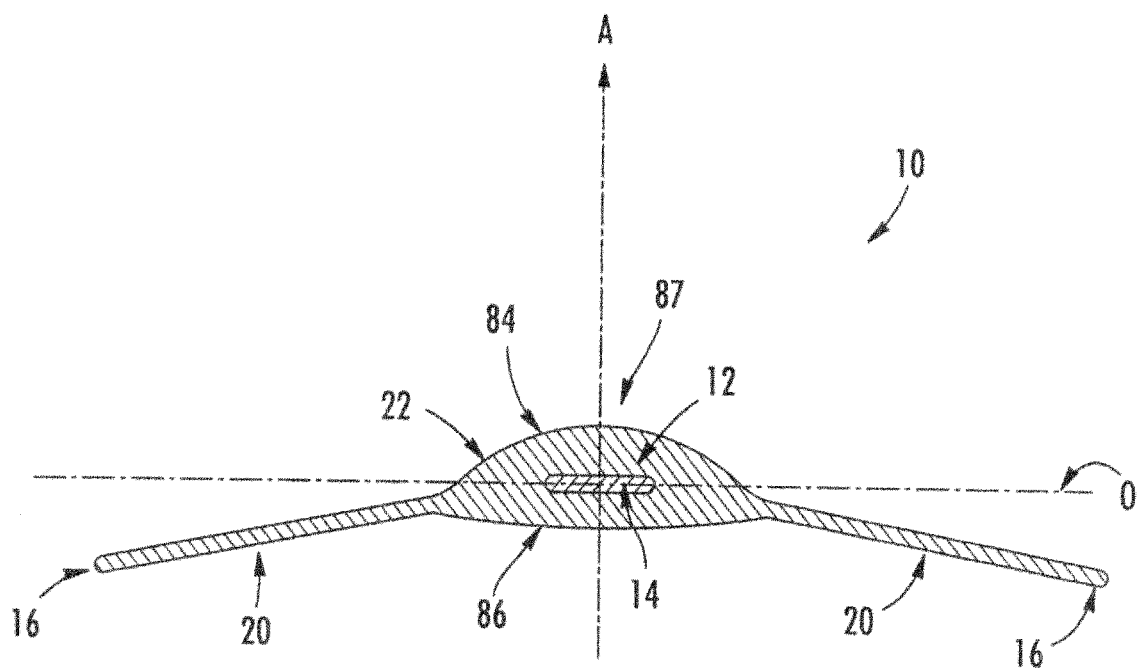
FIG. 18 shows a side elevation of an exemplary embodiment of implant 10 featuring a plano-convex type optic portion 12.

Referring to FIG. 18, in various embodiments, optic portion 12 comprises an anterior optical surface 84 and posterior optical surface 86. The combination of surface 84 and surface 86 may result in the optic being substantially planar, convex, plano-convex (illustrated in FIG. 18) and concave, bi-convex, concave-convex, or other known form. The diameter of optic portion 12 can vary as needed to accommodate the angle-to-angle measurement of the eye and curvature of the eye. In typical applications, the overall length of implant 10 (optic and haptics) to be inserted into an individual patient's eye is determined by adding a 1 mm white-to-white measurement of the patient's eye. In one embodiment, optic portion 12 has a 6 mm optical zone.

Optic portion 12 may be ground to the required diopter measurements necessary for vision correction. Optic portion 12 may form a lens, and the lens may be a negative or positive meniscus lens and may include correction for astigmatism. Depending on the refractive index of the material used, and the required vision correction, optic portion 2 may have the same thickness at central portion 87 and circumferential edge 22, or central portion 87 may be thinner than circumferential edge 22. In one embodiment, the thickness of optic 12 is 1 mm.

In some embodiments, implant 10 is designed to be foldable to facilitate insertion through small incisions, e.g., 3 mm in length or less. The device can be folded in the optic body, at any point in the flexible haptics, at the junction points between the optic body and the flexible haptics, or all of the above. The device can be folded with single or multiple folds along any direction.

Implant 10 can be usefully implanted into the eye as either a refractive phakic intraocular lens assembly or an aphakic intraocular lens assembly. Phakic intraocular lens implantation is becoming more popular because of their good refractive and visual results and because they are relatively easy to implant in most cases (Zaldivar & Rocha, 36 Int. Ophthalmol. Clin. 107-111 (1996); Neuhann et al., 14 J. Refract. Surg. 272-279 (1998); Rosen & Gore, 24 J. Cataract Refract. Surg. 596-606 (1998); Sanders et al., 24 J. Cataract Refract. Surg. 607-611 (1998)). The implantation can be performed by an ordinarily skilled ophthalmologist. Little surgical injury occurs to the ocular tissues during such implantation. When the surgical quality is not compromised, the results are highly predictable, immediate, and lasting.

For typical applications, suitable materials for implant 10 are solid, flexible, foldable optical, non-biodegradable materials such as hydrogel, collamer, collagel (hydrogel-collagen blends) acrylic polymers, polymethylmethacrylate (PMMA) and silicone polymers. The implant 10 may also be made of a composite of materials, i.e. where the flexible haptics are fabricated from one material and optic portion 12 from another material, for example, acrylic optics and hydrogel haptics. Where the lens assembly is used in the aphakic eye, flexible, but less foldable, materials may be preferred. For example, for the aphakic eye, the implant 10 may be made of all PMMA or a composite of PMMA optics and prolene haptics.

The implantation of implant 10 can generally be performed as provided by (Singh, eMedicine Ophthalmology (2000) http://www.emedicine.com/oph/topic662.htm).

First, the administration of local antibiotic drops is begun. A useful antibiotic is Tobramycin 0.3%, 1 drop, 6 times a day. Then, the pupil of the eye is contracted with 1% pilocarpine drops, administered for example at 15-minute intervals, starting 45 minutes before surgery. Drops (such as NSAID drops) are administered 2 times before surgery to minimize inflammation.

General anesthesia can be performed on the patient, but local anesthesia is preferred. For local anesthesia, 2% lidocaine with 7.5 U/ml hyaluronidase can be given 10 minutes before surgery. Orbital compression is applied to make the eye soft and to reduce orbital pressure.

For preparation of the surgical field, the periorbital skin of the patient is painted with iodine, then 5% povidine is applied. 5% povidine is also applied two-three times to the lid margin and the conjunctival fornices. Then, the eye is washed with saline.

An eye speculum is used for exposure of the surgical field. Upper and lower lid sutures, as well as superior rectus sutures can be applied in place of the speculum. (A sutureless procedure can also be used.) Adhesive plastic, applied to the surface of the eyelids, is used to pull the eyelashes.

For making small intraoperative incisions, a side port (for example, 0.6 mm) is made in the anterior chamber. This injection is started at the opposite limbus. As the aqueous fluid drains, it is replaced, for example, with a viscoelastic agent. The depth of the anterior chamber is not reduced at any time.

In one embodiment, for implantation of the implant 10 into the eye, two side ports are made to introduce the instruments that are used to fix the iris to the haptics. The width of the incision depends on the diameter of the intraocular lens assembly of the invention (being, for example, 4-5 mm). The incision may be made at the limbus or in the clear cornea. If a pocket section is made, wound closure (see, below) can be made without sutures. The intraocular lens assembly of the invention can then be introduced in the pre-crystalline space with angled-suture forceps the lens is positioned, for example, behind the iris on a horizontal axis with a cyclodialysis spatula. The intraocular lens assembly of the invention is then manipulated to center the optic on the pupil. During implantation of implant into the anterior chamber, the lens is centered and fixed so that it does not slip out of position. The lens can be positioned between the cornea and the iris, but avoiding contact with either to prevent corneal damage, proliferation of corneal epithelium on the anterior surface of the lens causing opacification, or iris. If the lens is not positioned properly with respect to the pupil, too much light may be admitted to the retina, causing serious vision difficulties. The haptics generally lodge as described above. Also, the anterior chamber of the eye is filled with the aqueous humor, a fluid secreted by the ciliary process, passing from the posterior chamber to the anterior chamber through the pupil, and from the angle of the anterior chamber it passes into the spaces of Fontana to the pectinate villi through which it is filtered into the venous canal of Schlemm. The implanted lens is positioned so the flow of fluid is not blocked.

After implant 10 is implanted, the viscoelastic material (if previously introduced into the eye chambers) is removed from the anterior and posterior chambers of the eye with an aspiration syringe (such as a 24-gauge cannula). Implant 10 is fixed and centered by the haptics of the lens as described in the examples above. The anterior chamber is washed thoroughly with saline. The pupil is contracted with intraocular acetylcholine 1%, carbachol 0.01%, or pilocaipine 0.5% solution. The incision is closed by hydrating the corneal incisions. A suture rarely is needed.

In another embodiment, for implantation of implant 10, the main incision is made at the ventral area of the eye (at the "top" of the eye, at "12 o'clock"). The width is preferably equal to the size of the optic, which may be 4-5 mm. Side incisions are made, approximately 1 mm wide. Implant 10 is inserted then vertically. Implant 10 rotated inside the viscoelastic-filled anterior chamber; the haptics are placed horizontally as in the examples provided above.

In some embodiments, fixating implant 10 may be a bimanual procedure. Implant 10 may be implanted using special tools to compress the haptics, such as forceps or cannulae, or may rely on microhooks to manipulate the optic through a hole in the surface of the optic (see discussion in U.S. Pat. No. 6,142,999). A vertically-holding lens forceps, which enters the anterior chamber through the main incision, centers the optic on the pupil and holds it steadily. A thin forceps is introduced from the side incision and grasps the iris close to the claw, allowing manipulation of the iris, and/or fixation of one or more of the haptics, for example, in the configurations described above. Both instruments are withdrawn, and the surgeon changes hands for holding each tool. The anterior chamber of the eye is again deepened with viscoelastic material, and the lens-fixation instruments are reintroduced. A second haptic-fixation maneuver may then be performed through the incision on the opposite side. Accordingly, implant 10 may be centered and fixated using the techniques described above, providing accommodation for the patient.

A peripheral iridectomy can then be performed. Then, the introduced viscoelastic material (if any) is aspirated through the three incisions. The anterior chamber is gently irrigated and inflated with air to remove all viscoelastic material.

For closure of the incision line, the apposition of the sides of the incision may be achieved by one or two superficial sutures. Alternatively, a large air bubble may be left inside the anterior chamber to effect an apposition. If the limbal incision was made without a pocket, then a closure of the incision line should be performed using sutures.

At the end of the surgery, 20 mg of gentamycin and 2 mg of dexamethasone are subconjunctivally injected. A sterile pad and a protective shield are applied.

In some embodiments, the intraocular lens assembly of the invention can be located in the posterior chamber of the eye, using methods known to those of skill in the ophthalmic art.

Aphakic implantation is also usefully provided for by implant 10. As noted above, the lens assembly can be surgically implanted outside or inside of the evacuated capsular bag of the lens of an eye. When implanted inside the capsular bag (for example, through the anterior capsule opening in the bag), implant 10 may be placed in a position such that optic portion 12 is aligned with the opening defined by the anterior capsular remnant. Implant 10 may be centered and fixated using the techniques described above, providing accommodation for the patient.

Advantageously, in some embodiments post-operative atropinization of the optic ciliary muscle is not required for implant 10 (when implanted either as a refractive phakic intraocular lens or an aphakic intraocular lens) to achieve accommodation. During surgery, especially for implantation of aphakic intraocular lenses, the ciliary muscle of the eye had previously and typically been paralyzed with a ciliary muscle relaxant to place the muscle in its relaxed state. Ciliary muscle relaxants include anticholinergics such as atropine, scopolamine, homatropine, cyclopentolate and tropicamide. Atropine is preferred. Proprietary preparations of atropine include Isopto Atropine (eye drops); Minims Atropine Sulphate (single-dose eye drops); Min-I-Jet Atropine (injection); Actonorm Powder (combined with antacids and peppermint oil); Atropine-1; Atropine-Care; Atropisol; Isopto Atropine; Ocu-tropine; Atropair; Atropine Sulfate S.O.P.; Atrosulf; 1-Tropine; Isopto Atropine; and Ocu-Tropine. Prior to this invention (i.e., while implanting intraocular lenses not having the advantages of the foldable intraocular lens assembly of the invention), the patient's eye would be atropinized following surgery, to allow for accommodation of the lens of the implanted aphakic intraocular lens assembly to the eye (see discussion, U.S. Pat. No. 6,051,024). Following surgery, the ciliary muscle relaxant (such as atropine) would be periodically introduced throughout a post-operative fibrosis and healing period (such as two to three weeks) to maintain the ciliary muscle in its relaxed state until fibrosis was complete. This drug-induced relaxation of the ciliary muscle prevented contraction of the ciliary muscle and immobilized the capsular bag. Thus, the implanted intraocular lens optic fixed during fibrosis in its distant vision position within the eye relative to the retina (accommodation). The implanted lens pressed backward against and thereby forwardly stretched the elastic posterior capsule of the capsular bag. By contrast, because of the haptic design of the intraocular lens assembly of the invention, the lens can, when fixated and centered using the techniques described above, provide accommodation for the patient without the administration of post-operative atropine.

It will be apparent to those skilled in the art that other changes and modifications can be made in the above-described invention and methods for making and using the same, without departing from the scope of the invention herein, and it is intended that all matter contained in the above description shall be interpreted in an illustrative and not in a limiting sense.

What is claimed is:

1. An accommodating intraocular implant apparatus for implantation in the human eye, comprising:
   an optic portion having a periphery and an optic axis, said optic portion lying substantially within an optic plane transverse to said optic axis; and
   at least two flexible haptics each extending from a point on the periphery of the optic portion, wherein the at least two flexible haptics are each a closed loop extending from the point on the periphery of the optic portion to a first portion of the eye and a second portion of the eye and returning to another point on the periphery of the optic portion, each closed loop comprises:
      at least two fixation anchors distal to the periphery of the optic portion, positioned a first distance from the center of the optic portion, and adapted to couple to the first portion of the eye; and
      at least one centering anchor distal to the periphery of the optic portion, positioned between the at least two fixation anchors and at a second distance, greater than the first distance, from the center of the optic portion, and adapted to couple to the second portion of the eye,
      wherein the at least two fixation anchors and the at least one centering anchor are coupled to the optic portion by the at least one flexible haptic.

2. The apparatus of claim 1, wherein:
   the optic axis is adapted for coaxial alignment with a vision axis of the eye;
   the first portion of the eye is the ciliary sulcus of the eye;
   the second portion of the eye is one of: a ciliary body, a ciliary muscle, or a ciliary zonule of the eye;
   at least one flexible haptic is adapted to connect the optic portion to the at least one centering anchor to maintain the coaxial alignment of the optic axis with the vision axis, and
   at least one haptic is configured to connect the optic portion to the at least two fixation anchors and, in response to ciliary muscle action in the eye, move the optic portion along the vision axis to provide accommodation.

3. The apparatus of claim 1, wherein the periphery of the optic portion comprises a circumferential edge which lies substantially in the optic plane, and each flexible haptic extends from the circumferential edge to each fixation anchor at an angle to the optic plane.

4. The apparatus of claim 3, wherein each flexible haptic extends away from the optic plane on a side of the optic plane adapted to face towards the posterior of the eye.

5. The apparatus of claim 3, wherein the at least one centering anchor lies substantially within the optic plane.

6. The apparatus of claim 1, comprising
   M centering anchoring portions, where M is a positive integer: and
   N fixation anchor portions, where N is a positive integer.

7. The apparatus of claim 6, where N is greater than 3.

8. The apparatus of claim 6, where N is greater than 7.

9. The apparatus of claim 1, wherein the at least two flexible haptics are integral with the optic portion.

10. The apparatus of claim 1, wherein the intraocular implant is foldable with one or multiple folds along any direction in the absence of a hinge.

11. The apparatus of claim 1, comprising a material selected from the group consisting of: hydrogel, collagen, collamar, collagel, acrylate polymers, methacrylate polymers, silicone polymers, and composites thereof.

12. The apparatus of claim 1, each of said haptics including:
   a first connecting portion extending between the periphery of the optic portion and the first fixation anchor;
   a second connecting portion extending between the first fixation anchor and a centering anchor;
   a third connecting portion extending between the centering anchor and the second fixation anchor; and
   a fourth connecting portion extending between the second fixation anchor and the periphery of the optic portion.

13. The apparatus of claim 12, wherein the periphery of the optic portion comprises a circumferential edge which lies substantially in the optic plane, and the first and fourth connecting portions extend from the circumferential edge at an angle to the optic plane.

14. The apparatus of claim 13, wherein the first and fourth connecting portion extend away from the optic plane on a side of the optic plane adapted to face towards the posterior of the eye when the intraocular implant is implanted.

15. The apparatus of claim 1, wherein each fixation anchor comprises one of: a serrated portion, a wedge shaped portion, a cylindrical portion, multiple connected wedge shaped portions, multiple connected cylindrical portions, a bar shaped portion.

16. A method for correcting vision in a human eye comprising:
   folding an accommodating intraocular implant with one or multiple folds along any direction in the absence of a hinge;
   implanting the accommodating intraocular implant in the eye, said intraocular implant comprising:
      an optic portion having a periphery and an optic axis, said optic portion lying substantially within an optic plane transverse to said optic axis; and
      at least two flexible haptics, wherein each flexible haptic is a closed loop extending from the point on the periphery of the optic portion to at least two fixation anchors, at least one centering anchor, and returning to another point on the periphery of the optic portion;
   coupling the at least ene two fixation anchors to a first portion of the eye; and
   coupling the at least one centering anchor to a second portion of the eye.

17. The method of claim 16, wherein the implanting comprises:
   coupling the at least one centering anchor to the ciliary sulcus of the eye;
   coupling the at least two fixation anchors to one of: a ciliary body, a ciliary muscle, a ciliary zonule of the eye.

18. The method of claim 17, wherein the implanting further comprises:
   making an incision in the eye;
   folding the accommodating intraocular implant into a folded state small enough to pass through said incision;
   passing the accommodating intraocular implant through the incision to a desired position within the eye;
   unfolding the accommodating intraocular implant to an unfolded state suitable for coupling to the eye.

19. The method of claim 18, further comprising removing the natural crystalline lens of the eye.

* * * * *